US012569597B2

(12) United States Patent
Schorgl et al.

(10) Patent No.: US 12,569,597 B2
(45) Date of Patent: Mar. 10, 2026

(54) METHODS FOR FORMING STENTS MODIFIED WITH MATERIAL COMPRISING AMNION TISSUE

(71) Applicant: Peytant Solutions, Inc., Plymouth, MN (US)

(72) Inventors: John Schorgl, Chanhassen, MN (US); Paul Thompson, Minnetonka, MN (US); Steven J. Healy, Vadnais Heights, MN (US); Robert Thatcher, Blaine, MN (US)

(73) Assignee: Peytant Solutions, Inc., Plymouth, MN (US)

( * ) Notice: Subject to any disclaimer, the term of this patent is extended or adjusted under 35 U.S.C. 154(b) by 262 days.

(21) Appl. No.: 18/372,975

(22) Filed: Sep. 26, 2023

(65) Prior Publication Data

US 2024/0009356 A1     Jan. 11, 2024

Related U.S. Application Data

(63) Continuation of application No. 14/941,127, filed on Nov. 13, 2015, now abandoned, which is a continuation of application No. 12/713,666, filed on Feb. 26, 2010, now Pat. No. 9,205,177.

(60) Provisional application No. 61/157,462, filed on Mar. 4, 2009.

(51) Int. Cl.

| | |
|---|---|
| *A61L 31/00* | (2006.01) |
| *A61F 2/06* | (2013.01) |
| *A61F 2/07* | (2013.01) |
| *A61F 2/82* | (2013.01) |
| *A61F 2/86* | (2013.01) |
| *A61L 27/36* | (2006.01) |
| *A61L 27/38* | (2006.01) |
| *A61L 27/50* | (2006.01) |
| *A61L 31/08* | (2006.01) |
| *A61L 31/14* | (2006.01) |
| *A61L 31/16* | (2006.01) |

(52) U.S. Cl.
CPC .............. *A61L 31/005* (2013.01); *A61F 2/07* (2013.01); *A61L 31/08* (2013.01); *A61L 31/148* (2013.01); *A61L 31/16* (2013.01); *A61F 2/062* (2013.01); *A61F 2002/065* (2013.01); *A61F 2/82* (2013.01); *A61F 2/86* (2013.01); *A61F 2210/0076* (2013.01); *A61F 2220/0025* (2013.01); *A61F 2220/0066* (2013.01); *A61F 2310/00982* (2013.01); *A61L 27/3604* (2013.01); *A61L 27/3813* (2013.01); *A61L 27/3834* (2013.01); *A61L 27/507* (2013.01); *A61L 2300/30* (2013.01); *A61L*

*2300/412* (2013.01); *A61L 2300/64* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 4,503,569 | A | 3/1985 | Dotter |
| 4,512,338 | A | 4/1985 | Balko et al. |
| 4,732,152 | A | 3/1988 | Wallsten et al. |
| 4,733,665 | A | 3/1988 | Palmaz |
| 4,739,762 | A | 4/1988 | Palmaz |
| 4,776,337 | A | 10/1988 | Palmaz |
| 4,829,000 | A | 5/1989 | Kleinman et al. |
| 4,848,343 | A | 7/1989 | Wallsten et al. |
| 4,950,227 | A | 8/1990 | Savin et al. |
| 5,019,090 | A | 5/1991 | Pinchuk |
| 5,100,429 | A | 3/1992 | Sinofsky et al. |
| 5,195,984 | A | 3/1993 | Schatz |
| 5,256,418 | A | 10/1993 | Kemp et al. |

(Continued)

FOREIGN PATENT DOCUMENTS

| | | |
|---|---|---|
| CN | 1927413 A | 3/2007 |
| EP | 0206025 A2 | 12/1986 |

(Continued)

OTHER PUBLICATIONS

Niknejad et al. "The effects of preservation procedures on amniotic membrane's ability to serve as a substrate for cultivation of endothelial cells", Cryobiology, vol. 63, Issue 3, 2011, pp. 145-151. (Year: 2011).*

(Continued)

*Primary Examiner* — Carlos A Azpuru
*Assistant Examiner* — Casey S Hagopian
(74) *Attorney, Agent, or Firm* — Christensen, Fonder Dardi PLLC; Peter S. Dari; Elizabeth A. Gallo

(57) ABSTRACT

A stent scaffold combined with amniotic tissue provides for a biocompatible stent that has improved biocompatibility and hemocompatibility. The amnion tissue can be variously modified or unmodified form of amnion tissue such as non-cryo amnion tissue, solubilized amnion tissue, amnion tissue fabric, chemically modified amnion tissue, amnion tissue treated with radiation, amnion tissue treated with heat, or a combination thereof. Materials such as polymer, placental tissue, pericardium tissue, small intestine submucosa can be used in combination with the amnion tissue. The amnion tissue can be attached to the inside, the outside, both inside and outside, or complete encapsulation of the stent scaffold. In some embodiments, at least part of the covering or lining comprises a plurality of layers of amnion tissue. The method of making the biocompatible stent and its delivery and deployment are also discussed.

18 Claims, 17 Drawing Sheets

(56) References Cited

U.S. PATENT DOCUMENTS

| | | | |
|---|---|---|---|
| 5,275,826 A | 1/1994 | Badylak et al. |
| 5,342,387 A | 8/1994 | Summers |
| 5,464,650 A | 11/1995 | Berg et al. |
| 5,612,028 A | 3/1997 | Sackier et al. |
| 5,693,085 A | 12/1997 | Buirge et al. |
| 5,876,432 A | 3/1999 | Lau et al. |
| 6,004,261 A | 12/1999 | Sinofsky et al. |
| 6,090,035 A | 7/2000 | Campbell et al. |
| 6,152,142 A | 11/2000 | Tseng |
| 6,241,691 B1 | 6/2001 | Ferrera et al. |
| 6,293,959 B1 | 9/2001 | Miller et al. |
| 6,326,019 B1 | 12/2001 | Tseng |
| 6,326,109 B1 | 12/2001 | Bourdelais et al. |
| 6,331,188 B1 | 12/2001 | Lau et al. |
| 6,391,052 B2 | 5/2002 | Buirge et al. |
| 6,475,232 B1 | 11/2002 | Babbs et al. |
| 6,508,833 B2 | 1/2003 | Pavcnik et al. |
| 6,638,317 B2 | 10/2003 | Nakao |
| 7,029,839 B2 | 4/2006 | Toledo-Pereyra et al. |
| 7,056,337 B2 | 6/2006 | Boatman |
| 7,137,947 B2 | 11/2006 | Sarac |
| 7,147,871 B2 | 12/2006 | Voytik-Harbin et al. |
| 7,211,108 B2 | 5/2007 | Furst et al. |
| 7,294,144 B1 | 11/2007 | Schneider |
| 7,326,241 B2 | 2/2008 | Jang |
| 7,351,421 B2 | 4/2008 | Sung et al. |
| 7,384,428 B2 | 6/2008 | Richter |
| 7,442,205 B2 | 10/2008 | Verhoeven et al. |
| 7,452,371 B2 | 11/2008 | Pavcnik et al. |
| 7,468,276 B2 | 12/2008 | Hariri |
| 7,494,802 B2 | 2/2009 | Tseng et al. |
| 7,824,671 B2 | 11/2010 | Binder et al. |
| 8,734,502 B2 | 5/2014 | Orr |
| 2001/0021871 A1 | 9/2001 | Stinson |
| 2001/0041928 A1 | 11/2001 | Pavcnik et al. |
| 2002/0143385 A1 | 10/2002 | Yang |
| 2003/0074049 A1 | 4/2003 | Hoganson et al. |
| 2004/0048796 A1 | 3/2004 | Hariri et al. |
| 2005/0187604 A1 | 8/2005 | Eells et al. |
| 2005/0220848 A1 | 10/2005 | Bates |
| 2006/0159641 A1 | 7/2006 | Girardot et al. |
| 2006/0217800 A1 | 9/2006 | Ganesan |
| 2007/0031471 A1 | 2/2007 | Peyman |
| 2007/0112411 A1 | 5/2007 | Obermiller et al. |
| 2007/0156232 A1 | 7/2007 | Kutryk et al. |
| 2008/0254092 A1 | 10/2008 | McDevitt et al. |
| 2009/0043371 A1 | 2/2009 | Fearnot |
| 2009/0204228 A1 | 8/2009 | Hiles |
| 2009/0258082 A1 | 10/2009 | Nikaido et al. |
| 2009/0276036 A1 | 11/2009 | Nagura et al. |
| 2009/0286220 A1 | 11/2009 | Sheleg et al. |
| 2010/0043802 A1 | 2/2010 | O'Brien et al. |
| 2010/0104539 A1 | 4/2010 | Daniel et al. |
| 2010/0124569 A1 | 5/2010 | Abbot et al. |
| 2010/0228335 A1 | 9/2010 | Schorgl et al. |
| 2011/0206776 A1 | 8/2011 | Tom et al. |
| 2012/0035527 A1 | 2/2012 | Tearney et al. |
| 2013/0344162 A1 | 12/2013 | Morse et al. |
| 2014/0050788 A1 | 2/2014 | Daniel et al. |
| 2014/0067058 A1 | 3/2014 | Koob et al. |
| 2014/0217649 A1 | 8/2014 | Kochevar et al. |
| 2016/0136334 A1* | 5/2016 | Schorgl ................... A61L 31/08 |
| | | 623/1.13 |

FOREIGN PATENT DOCUMENTS

| | | | |
|---|---|---|---|
| EP | 0230672 A2 | 8/1987 |
| JP | 2005-124996 A | 5/2005 |
| JP | 2008-200185 A | 9/2008 |
| WO | 89/07425 A2 | 8/1989 |
| WO | 00/38590 A1 | 7/2000 |
| WO | 2005/077433 A1 | 8/2005 |

OTHER PUBLICATIONS

Niknejad et al. "Properties of the amniotic membrane for potential use in tissue engineering", European Cells and Materials, vol. 15, 2008, pp. 88-99. (Year: 2008).*

Allie et al., "24-Carat Gold, 14-Carat Gold or Platinum Standards in the Treatment of Critical Limb Ischemia: Bypass Surgery or Endovascular Intervention?", J. Endovasc. Ther. 2009; 16:000-000.

Bhatia et al., "The Mechanism of Cell Interaction and Response on Decellularized Human Amniotic Membrane: Implications in Wound Healing", Wounds, 2007; 19 (8): 207-217.

Cloft et al., "Bovine Type I Collagen as an Endovascular Stent-Graft Material: Biocompatibility Study in Rabbits" Radiology 2000; 214:557-562.

Connolly et al., "Trigylcidylamine Crosslinking of Porcine Aortic Valve Cusps or Bovine Pericardium Results in Improved Biocompatibility, Biomechanics, and Calcification Resistance: Chemical and Biological Mechanisms," Am. J. Pathol. 2005; 166(1):1-13.

Dardik et al., "Arterial Reconstruction with a Modified Collagen Tube: A Clinical Experience," Ann. Surg. 1974; 180 (2):144-146.

Gris et al., "Application of Amniotic Membrane in Ocular Surface Pathology," Annals of Transplantation 1999; 4:82-84.

Gurinsky, "A novel dehydrated amnion allograft for use in the treatment of gingivial recession: An observational case series," Journal of Implant & Advanced Clinical Dentistry, vol. 1, No. 1, Mar. 2009, (9 pages).

"Inventions at UMDNJ Technology Highlights: Stem Cells and Tissue Engineering" University of Medicine & Dentistry of New Jersey, Office Of Patents and Licensing, 2006.

Jiang et al., "A Novel Intravascular Stents Covered with Human Amniotic Membrane," 2007 IEEE/ICME International Conference on Medical Engineering, pp. 1961-1964.

Niknejad et al., "Properties of the Amniotic Membrane for Potential Use in Tissue Engineering," European Cells and Materials 2008; 15:88-99.

Park et al., "Immunosuppressive Property of Dried Human Amniotic Membrane", Opthalmic Research, 2009; 41 :112-113; published online Dec. 20, 2008.

"RCA Success Story: Tissue Banking by Using Nuclear Techniques," http://www.rcaro.org/_sac2/sac/sucess%20story/RCA%20Success%20Story%20-%20Tissue%20Bank.doc.

Van Wachem et al., "In Vivo Behavior of Epoxy-Crosslinked Porcine Heart Valve Cusps and Walls," J. Biomed. Mater. Res. 2000; 53:18-27.

Wu et al., "Tissue-engineered microvessels on three-dimensional biodegradeable scaffolds using human endothelial progenitor cells," Am. J. Physiol. Heart Circ. Physiol. 287:H480-H487, 2004.

International Search Report and Written Opinion for International application No. PCT/US2010/025558, dated Oct. 28, 2010.

Office Action from co-pending Japanese application 2011-552993 dated Apr. 8, 2014 with translation.

European Search Report from co-pending European application 10749126.8 dated May 8, 2014.

U.S. Appl. No. 12/713,666, filed Feb. 26, 2010, now U.S. Pat. No. 9,205,177B2 (36 pages).

U.S. Appl. No. 14/941,127, filed Nov. 13, 2015, now U.S. Pat. No. 2016/0136334A1 (34 pages).

Appeal Brief for U.S. Appl. No. 14/941,127, filed May 4, 2020 (27 pages).

Examiner's Answer for U.S. Appl. No. 14/941,127, notification Jul. 29, 2020 (10 pages).

Reply Brief for U.S. Appl. No. 14/941,127, filed Sep. 28, 2020 (6 pages).

Decision on Appeal for U.S. Appl. No. 14/941,127, notification Jun. 22, 2021 (12 pages).

Appeal Brief for U.S. Appl. No. 14/941,127, filed Sep. 20, 2022 (29 pages).

Examiner's Answer for U.S. Appl. No. 14/941,127, notification Oct. 27, 2022 (15 pages).

Reply Brief for U.S. Appl. No. 14/941,127, filed Dec. 21, 2022 (9 pages).

Record of Oral Hearing for U.S. Appl. No. 14/941,127, notification Jul. 27, 2023 (16 pages).

(56)           References Cited

OTHER PUBLICATIONS

Decision on Appeal for U.S. Appl. No. 14/941,127, notification Jul. 28, 2023 (15 pages).

Fénelon et al., "Applications of Human Amniotic Membrane for Tissue Engineering", Membranes, 11(387), p. 1-27, (2021).

* cited by examiner

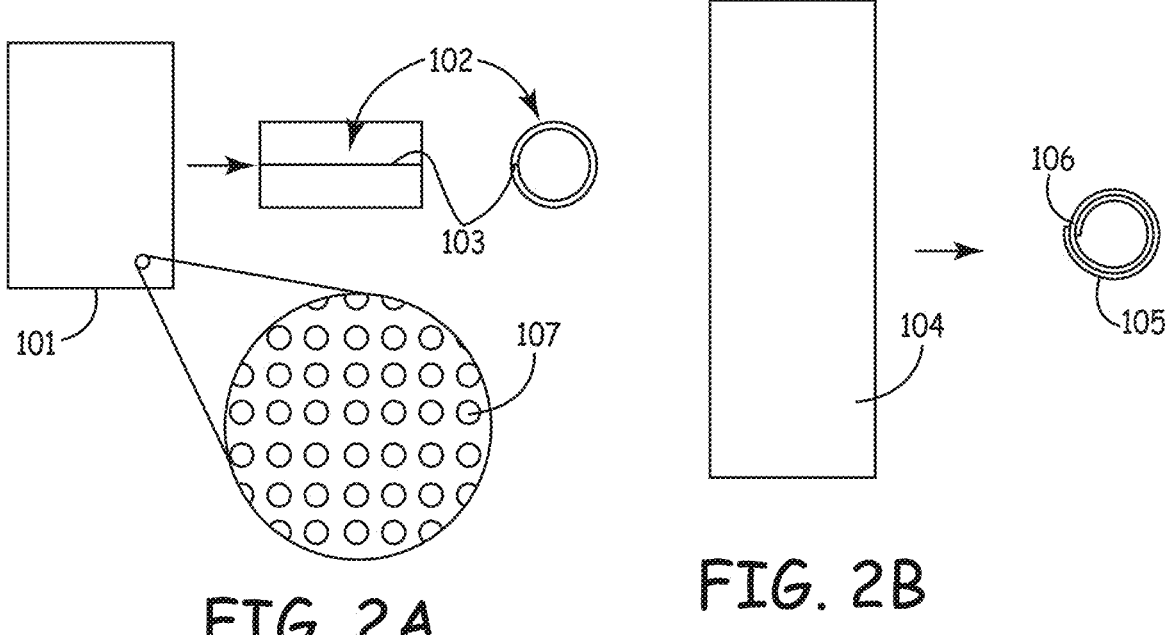
FIG. 2A
FIG. 2B
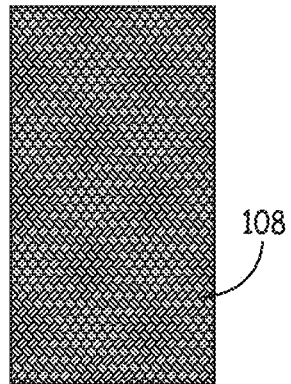
FIG. 2C

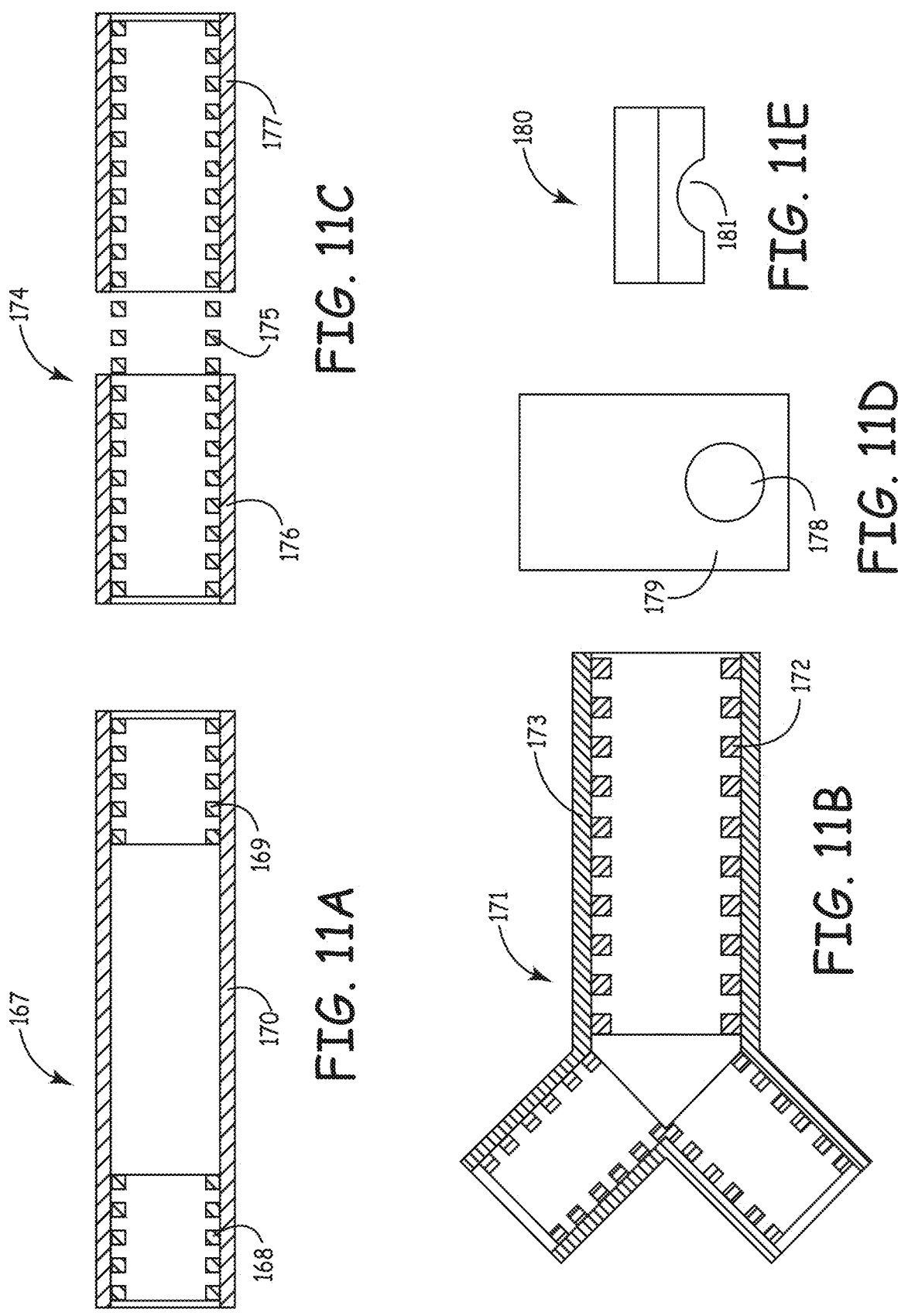

235

236

METHODS FOR FORMING STENTS MODIFIED WITH MATERIAL COMPRISING AMNION TISSUE

CROSS REFERENCE TO RELATED APPLICATIONS

This application is a continuation of copending U.S. patent application Ser. No. 14/941,127 filed Nov. 13, 2015 to Schorgl et al., entitled "Stents Modified with Material Comprising Amnion Tissue and Corresponding Processes," which is a continuation of corresponding U.S. patent application Ser. No. 12/713,666 filed Feb. 26, 2010, (now U.S. Pat. No. 9,205,177) to Schorgl et al., entitled "Stents Modified with Material Comprising Amnion Tissue and Corresponding Processes," which claims benefit of provisional patent application Ser. No. 61/157,462 filed on Mar. 4, 2009 to Schorgl et al., entitled "Stents Covered or Coated With Amnion Tissue and Methods," incorporated herein by reference.

FIELD OF THE INVENTION

The inventions in general are related to using material comprising amnion tissue to modify stents. The inventions are further related to methods of using amnion tissue to modify stents.

BACKGROUND

Stents are widely used in interventional cardiology, interventional radiology, gastrointestinal medicine, and pulmonary medicine. Stents in general can be used to open constricted lumens. The implantation of stents however is known to risk restenosis. For example, bare metal coronary stents are known to have a restenosis rate generally greater than 15-30% at one year after deployment in small vessels. Drug eluding coronary stents have reduced the 12 month restenosis rates to the low single digits. Drug eluting stents have however poses new clinical risks such as delayed re-endothelization. Late endothelization of coronary stents has been observed to result in a 12 month subacute thrombosis rate of 1-2%. Subacute thrombosis of drug eluting coronary stents can be fatal in a significant number of the patients in whom it occurs.

SUMMARY OF THE INVENTION

In one aspect, the invention relates to a biocompatible stent for placement in a vessel of a living subject. The stent comprises a stent scaffold and a biocompatible material associated with the stent scaffold. The biocompatible material comprises reconstituted amnion tissue, amnion tissue that has not been cryo-preserved at a temperature of –60 to –100° C., or a combination thereof. In some embodiments, the reconstituted amnion tissue comprises solubilized amnion tissue, a fabric fabricated from weaving, braiding, or knitting of amnion suture, filaments, or yarns, chemically modified amnion tissue, amnion tissue treated with radiation, amnion tissue treated with heat, or a combination thereof. In some embodiments, the biocompatible material is attached to the inside, the outside, or both inside and outside of the stent scaffold. In one embodiment, the biocompatible material comprises an amnion tissue covering or lining. In some embodiments, the biocompatible material comprises a plurality of layers of amnion tissue. In one embodiment, the biocompatible stent further comprises a thrombolytic agent, an anti-restenosis agent, cellular material, or a combination thereof. In one embodiment, the cellular material is stem cells. In some embodiments, the biocompatible material further comprises small intestinal submucosa tissue, pericardium tissue, placental tissue, polymeric material, or a combination thereof. In some embodiments, the stent scaffold comprises metal, alloy, polymer, or a combination thereof. In one embodiment, the stent scaffold is bio-absorbable. In some embodiments, the stent scaffold is bifurcated, segmented, continuous, crimped or a combination thereof. In some embodiments, the amnion tissue used comprises amnion epithelia cells.

In a second aspect, the invention relates to another biocompatible stent for placement in a vessel of a living subject. The other biocompatible stent comprises a stent scaffold and a biocompatible material comprising amnion tissue that substantially completely encapsulates the stent scaffold. In some embodiments, the amnion tissue comprises solubilized amnion tissue, a fabric fabricated from weaving, braiding, or knitting of amnion suture, filaments, or yarns, chemically modified amnion tissue, amnion tissue treated with radiation, amnion tissue treated with heat, or a combination thereof. In one embodiment, the stent scaffold is encapsulated with a coating of solubilized amnion tissue. In some embodiments, the biocompatible material comprises a covering, a lining, or a combination thereof. In some embodiments, at least part of the covering or lining comprises a plurality of layers of amnion tissue. In some embodiments, the biocompatible material further comprises small intestinal submucosa tissue, pericardium tissue, placental tissue, polymeric material, or a combination thereof. In one embodiment, the biocompatible stent is bio-absorbable. In some embodiments, the biocompatible stent further comprises a thrombolytic agent, an anti-restenosis agent, cellular material, or a combination thereof. In some embodiments, the amnion tissue used comprises amnion epithelia cells.

In a third aspect, the invention relates to a method for modifying a stent scaffold for placement in a vessel of a living subject. The method comprises the step of associating a processed biocompatible material with the stent scaffold. The processed biocompatible material is processed from a biocompatible material that comprises reconstituted amnion tissue, amnion tissue that has not been cryo-preserved at a temperature of –60 to –100° C., or a combination thereof. In some embodiments, the biocompatible material is processed by a method to form a covering or lining and the associating step comprises attaching the covering or lining to the inside, outside, or both inside and outside, of the stent scaffold. In one embodiment, the covering or lining comprises multiple layers of processed biocompatible material. The covering or lining can be attached to the stent scaffold via mechanical, electronic, adhesive, energy based method, or a combination thereof. In one embodiment, the biocompatible material is processed by a method comprising mechanically, chemically, or enzymatically break up amnion tissue to form a solubilized amnion tissue. The solubilized amnion tissue is then associated with the stent scaffold by (1) covering at least a part of the stent scaffold with the solubilized amnion tissue and (2) allowing the solubilized amnion tissue covered scaffold to dry to form a coating on the stent scaffold. In another embodiment, The solubilized amnion tissue is then associated with the stent scaffold by (1) covering at least a part of the covering or lining of a already covered or lined stent scaffold with the solubilized amnion tissue and (2) allowing the solubilized amnion tissue covered covering or lining to dry to form a coating on the covering or lining. In some embodiment, the biocompatible material is processed by a method comprising making an amnion fabric from weaving, braiding, or knitting of amnion suture, filaments, or yarns and the associating step comprises associating the amnion fabric with the stent scaffold.

In a fourth aspect, the invention relates to another method for modifying a stent scaffold for placement in a vessel of a living subject. The method comprises effectively completely encapsulating the stent scaffold with a processed biocompatible material that is processed from a biocompatible material that comprises amnion tissue. In some embodiments, the processed biocompatible material is formed in a method comprising forming a covering or lining from the biocompatible material and the encapsulating step comprises covering the stent scaffold with the covering or lining via mechanical, electronic, adhesive, energy based method, or a combination thereof. In one embodiment, the biocompatible material is processed by a method comprising mechanically, chemically, or enzymatically break up amnion tissue to form a solubilized amnion tissue. The stent scaffold is then encapsulated with the solubilized amnion tissue by (a) covering the stent scaffold with solubilized amnion tissue (b) allowing solubilized amnion tissue covered stent scaffold to dry to form a coating on the stent scaffold.

In a fifth aspect, the invention relates to a method of deploying the biocompatible stent comprising delivering the biocompatible stent into the site of treatment and deploying the stent into a deployed configuration. In some embodiments, the biocompatible stent is self-expanding. In one embodiment, the biocompatible stent is deployed by a balloon. In some embodiments, the method further comprises treating the site of treatment prior to the stent delivery.

In a sixth aspect, the invention relates to a biocompatible stent that comprises a stent scaffold and a biocompatible material comprising placental tissue that is associated with the stent scaffold.

BRIEF DESCRIPTION OF THE DRAWINGS

FIG. 2A is a set of drawings showing an amnion membrane being rolled into a tube with side and cross-sectional views of the tube showing a butt seam, the membrane optionally comprises holes that are shown through an enlarged portion of the membrane.

FIG. 2B is a set of drawings showing a long amnion membrane being rolled into a tube having two layers and a butt seam.

FIG. 2C is a top view of an amnion fabric made by weaving, braiding, or knitting of amnion suture, filaments, or yarns.

FIG. 11A is a sectional side view of an amnion sheet with stent scaffolds inside and a free unsupported amnion sleeve at the center.

FIG. 11B is a sectional side view of a bifurcated stent with an amnion sheath covering the exterior of a stent scaffold.

FIG. 11C is a sectional side view of two amnion sleeves on the end portions of a stent scaffold with the middle portion of the stent scaffold not covered.

FIG. 11D is a side view of an amnion sheet with a side hole to allow for side branch perfusion of blood or fluid FIG. 11E is a side view of the sheet of FIG. 10D rolled into tube with a butt joint.

DETAILED DESCRIPTION OF PREFERRED EMBODIMENTS

Figure 1:
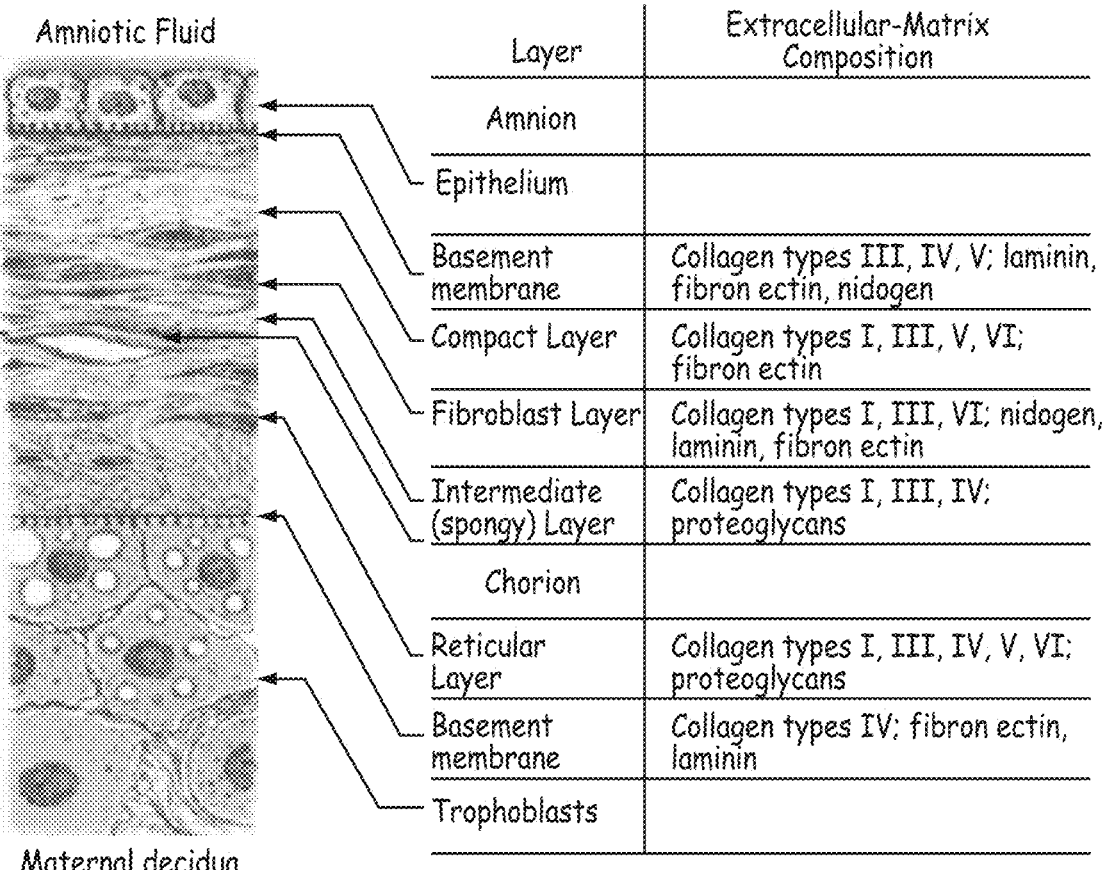
FIG. 1 is a schematic presentation of the structure of the fetal membrane at term showing layer of the extracellular matrix components.

Stents described herein comprise a stent scaffold modified with an amnion tissue such that the stent provides an improved surface for contact with the patient's native tissues. A stent scaffold modification described herein provides a biocompatible stent with associated amnion tissue for use in arteries, e.g., coronary arteries, as well as for use in other lumens within the human body. Stent scaffolds can be modified, for example, with amnion tissue that is derived from amniotic sac of the placenta. Amnion tissue provides a surface with low or no antigenicity such that the tissue provides a uniquely appropriate material for the colonization of the material with native cells from the patient, such as endothelial cells. The stents generally are designed to facilitate the opening of a vessel lumen while providing for flow through the vessel, although other stent structures can be similarly modified. In some embodiments, the stents can have a generally cylindrical shape. The stent scaffold is a structural element that supports the modifying tissue in the resulting stent product. Stent scaffolds modified with amnion tissue are believed to improve the biocompatibility of stents, lower restenosis rates after modified stent implantation, and favor re-endothelization of the treated blood vessel segment. In some embodiments, the stent scaffold can be coated with the tissue so that the entire surface exposed to the blood vessel is associated with amnion tissue. Also, desirable methods for handling and processing the amnion tissue for attachment to the stent scaffold are described. Improved re-endothelialization of the stent can be expected to reduce thrombosis associated with the stent with a corresponding improvement in the clinical results.

The stents described herein can be used in treatment involving vessel support, graft, and healing. For example, the biocompatible stent can be used in the treatment of abdominal aortic aneurysms (AAA) or as emboli coils. Additionally, in some embodiments, the biocompatible stent can be used for treatment procedures involving biological vessels, including coronary arteries and veins, peripheral arteries and veins, renal vessels, urethra and ureter, biliary duct, tracheal vessel, bronchial vessel, esophageal vessel, carotid vessel, intra cranial vessel, neurovascular vessel, vaginal vessel, and venous system. In some other embodiments, the biocompatible stent described herein can be used for treating: stent restenosis, and blood vessel occlusion. In some embodiments, the biocompatible stent can be used or adapted for use, for example, as: left atrial appendage (LAA) device if the stent is crimped to restrict flow through the stent, transjugular intrahepatic portosystemic shunt (TIPS), arteriovenous (A/V) grafts, treatment for patent foramen ovale (PFO), treatment for patent ductus arteriosus (PDA), treatment for atrial septal defects (ASD), and treatment for ventricular septal defects (VSD). Biocompatible, as used herein, refers to a material that is effectively non-toxic, sterile upon delivery to the patient and effectively non-thrombogenic upon exposure to blood.

Placental tissue comprises two major membrane components, the amnion and the chorion with the amnion being interior to the chorion in relation to the amniotic sac that encloses a mammalian, e.g., human, embryo. The layers are shown in FIG. 1. As described herein, the amnion layer of the amniotic sac can be separated from the chorion to be used directly. The side of the separated amnion tissue with the epithelium layer is generally referred to as the front side while the side with the extracellular matrix composition is generally referred as the back side. Alternatively, placental tissue, which contains both the amnion layer and the chorion layer, can be used to make a tissue for association with a stent scaffold. The side of the placental tissue with the amnion layer is generally referred to as the front side while the side with the chorion layer is generally referred as the back side. As used herein, the term "amnion tissue" refers to the amnion layer of the amniotic sac, a portion thereof, or any material including or derived from the amnion layer. When used as the covering or linings of a stent scaffold. The front side of the amnion tissue may face away from the stent scaffold. Although in some embodiments, the back side of the amnion tissue facing the stent scaffold may be more desirable. The term "placenta tissue" refers to any material comprising a composition from the amniotic sac, such as the amnion layer, the chorion layer, portions thereof or combinations thereof. In general, the front layer of the placental tissue facing away from the stent scaffold is a generally preferred configuration. Amnion tissue is particularly desirable for the applications described herein because amnion tissue can be expanded generally without damaging the tissue, and such expansion is generally associated with deployment of a stent scaffold as described herein. Suture, filaments or yarns containing amnion tissue material may be woven, braided or knitted to form a tissue-based fabric, which in turn can be used to form stent scaffold coating, such as a covering and/or lining. Small intestinal submucosa, pericardium, placental arteries and veins may be used as material alternative or in additional to amnion tissue to modify stent scaffold. In some embodiments, polymeric material may be used in conjunction with amnion tissue as well.

Stents described herein generally comprise a stent scaffold that provides a framework for the stent and a tissue material supported by the stent scaffold. In some embodiments, the tissue can be formed into a sleeve or the like for association with the stent scaffold. The amnion tissue used to construct a sleeve or other structure for association with a stent scaffold may be fresh (non-crosslinked), crosslinked, or partially crosslinked. The amnion tissue may be formed into a layer, such as a covering, lining or the like, to be attached to a stent scaffold. The covering or lining of amnion may be mechanically attached (hooks, rivets, staples), adhesive bonded, crosslinked, laser welded, ultrasonically welded, RF welded, pressure fit, interlocking with stent scaffold, or a combination thereof.

While generally cylindrically shaped stent scaffolds can be desirable for placement in various body vessels, other shapes can be conveniently used for some applications. In particular, in some application, it can be desirable to block flow rather than for use in opening and/or maintaining flow. Thus, in some embodiments, the stent can be crimped or otherwise constrained either at an end and/or between the ends to restrict or block flow. The occlusive embodiments can be desirable for example, as left atrial appendage devices which fit into a left atrial appendage of a heart to limit blood flow into the appendage. A crimped stent can be self expanding such that the released stent conforms to the location of placement while the crimping maintains partially or fully occluded configuration of the device.

The stent scaffold used can be self expandable or be expanded by another component such as a balloon. Stent scaffolds can be designed based on extensive knowledge in the art regarding stent formation. In general, the stent scaffold is deployed within the patient into a more extended configuration. In some embodiments of particular interest, the stents are vascular stents designed to facilitate the opening of a blood vessel that is at least partially occluded. Such vascular stents are generally cylindrical in shape with an initial deployment configuration and a deployed configuration that has a greater diameter. Amnion tissue is expandable relative to other types of tissue so that amnion tissue can better adapt to the deployment of a stent with less risk of tearing and/or other damage to the tissue.

The stent scaffold may be formed from polymeric, metallic, or a combination of polymer and metal materials. Suitable materials, in particular, can comprise spring metals that can undergo significant expansion of the structure without excess strain on the material. Suitable metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, Nitinol®, a nickel-titanium alloy, and combinations thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone, other copolymers and mixtures thereof. A very large number of vascular stent designs are known, and these designs can be adapted for use as stent scaffolds for the stents described herein. Representative vascular stents are described, for example, in published U.S. patent application 2009/0276036 to Nagura et al., entitled "Stent", U.S. Pat. No. 7,326,241 to Jang, entitled "Intravascular Stent", and U.S. Pat. No. 7,442,205 to Verhoeven et al., entitled "Stents, and Methods for Preparing Stents From Wires Having Hydrogel Coating Layers Thereon," all three of which are incorporated herein by reference.

The stent scaffold may have eyelets in the stent mesh or at the ends of the stent scaffold body to provide for suture anchoring locations. Alternatively, the stent scaffold may have a longitudinal bar containing eyelets for suture anchoring. In some embodiments, the stent scaffold may comprise radiopaque markers, which can be formed from platinum-iridium or platinum-tungsten or through radio-pacifiers, such as barium sulfate, bismuth trioxide, bismuth subcarbonate, powdered tungsten, powdered tantalum or the like, added to a polymer. The biocompatible stent formed from stent scaffold modified with placental tissue may be delivered using a catheter device and any associated delivery tools. For self expanding biocompatible stents, the stents maybe covered while being loaded on a catheter to be delivered inside a vessel. Alternatively, a balloon catheter may be used to deliver balloon expandable modified stents.

In general, tissue can be associated with a stent scaffold to coat the interior of the stent scaffold, the exterior of the stent scaffold, the ends of the stent scaffold or portions thereof. Similarly, since stent scaffolds can have an open structure, the stent scaffold can be embedded in a tissue to form the coated stent. In some embodiments, it is particularly desirable to coat an entire surface and two ends of the stent scaffold, and it may be desirable to coat the interior, the exterior and the ends to provide a particularly desirable surface to contact bodily tissues, including both the vessel wall and the blood. For example, the ends of a stent scaffold can provide surfaces for thrombus formation such that the covering of the ends of the stent scaffold can be desirable. The stent designs include effective designs that can both stabilize the stent with respect to reducing restenosis since the surfaces provide for colonization of native cells that can avoid inflammatory responses that can cause restenosis as well as reducing exposed surfaces that can induce thrombus formation that can result in emboli that can migrate downstream with corresponding risk to the patient.

A tissue layer for association with a stent scaffold may be made, for example, from a sheet of amnion tissue, a material constructed from amnion tissue, such as a fabric or the like, or reconstituted tissue may be coated onto the stent scaffold from a liquid amnion tissue solution by spraying, dip coating, using an electrophoretic technique, or the like. The liquid amnion tissue solution may be formed from amnion tissue, e.g., amnion tissue, through chemical digestion, enzymatic digestion, mechanical break up, or a combination thereof. The stent scaffold mesh may be encapsulated to provide for a smooth inner and/or outer surface. Additionally, a sleeve of amnion tissue may also be sandwiched between two stent scaffolds. The stent scaffolds sandwiching the amnion tissue sleeve may additionally have other amnion tissue embedding the stent mesh. In some embodiments, stent scaffolds can be encased in an amnion tissue covering at both ends of the covering while the center of covering is free of the stent scaffold support. To allow for special fluid perfusion, a stent scaffold can have two outer sleeves of tissue covering both of the end portions of the stent scaffold to allow for perfusion through the central portion of the stent scaffold to a branch vessel. Bifurcated stent scaffold may also be used to construct a bifurcated biocompatible stent. A plurality of amnion tissue layers maybe used to cover or line the stent scaffold. Covered or lined stent scaffold may be additionally coated with amnion tissue. Alternatively, coated stent scaffold may additionally be covered or lined with amnion tissue.

In terms of the covering and/or lining formation, amnion tissue can be rolled, for example, into a tube with a longitudinal seam. The tube can be used as a covering to cover the exterior of a stent scaffold or as a lining to line the interior of the stent scaffold. In some embodiments, both exterior and the interior of stent scaffold can be covered and lined, and a cuff or other tissue structure can be used to cover the ends of the stent scaffold. The amnion sheet constructed may have a side hole to allow for side branch perfusion of blood or fluid. This is desirable when the stent is placed adjacent a branch vessel. The exterior covering or inner lining may alternatively be attached to the stent scaffold by rolling the covering or lining over the ends of the stent scaffold to form a cuff. The longitudinal seam of the covering or lining of the tissue tube may be butt seamed or lap seamed. The seam may be joined by sewing, gluing, ultrasonic welding, laser welding, thermo bonding, or using clips, staples, fish hook like barbs, rivets. The seam may be zigzag, sinusoidal, circumferential helical and square notched in shape. The seam can have male and female interlocking joints or may have a series of belts and slots to join together.

The tissue covering or lining may contain holes that are round, oval, square or slots or other suitable shape. The holes can be from 5 microns to 1000 microns in average diameter. The holes can increase the rate of tissue in-growth. The holes may also be loaded with drugs such as heparin, Taxol, Rapamycin or other suitable drugs for suitable applications. The amnion tissue can be rich with stem cells. The stem cells may assist with the growth of endothelial cells on inner lumen of the device. Amnion tissue can be used two ways, i.e. with viable cells and without viable cells. The epithelium layer of the amnion tissue may be removed or left intact for the covering or lining.

Additionally or alternatively, the stent scaffold or covered or lined stent can be coated with a tissue solution. Placental tissue, e.g., amnion tissue, can be dispersed by chemical, enzymatic or mechanical means to form a solution. The tissue solution can be coated or sprayed onto the stent scaffold or covered or lined stent. The scaffold maybe rotated while the spaying is performed. In some embodiments, the stent scaffold maybe loaded on a mandrel while being sprayed by an amnion solution. The amnion solution may additionally be used as adhesive means to attach amnion covering or lining to a stent scaffold. In some embodiments, a modified stent scaffold with an inner sleeve of amnion can additionally have an outer coating of amnion made from the amnion solution described herein.

In general, regardless of the particular stent structure, the tissue modified stents can generally be deployed by adapting techniques developed for stent deployment of conventional stents. Thus, for example, the tissue modified stent can be placed over a deflated balloon on a delivery catheter. Once in position, the balloon can be inflated to expand the stent. The balloon can be inflated additional times if desired to provide the desired degree of stent expansion. Once the balloon is deflated, the catheter can be removed, and the stent can be left in a deployed configuration within a vessel. Furthermore, a self-expanding stent can be deployed from a sheath. The tissue modified stent can be placed within the sheath in a deployment configuration. The sheath can be withdrawn from covering the stent such that the stent can self-expand into a deployed configuration. The sheath can be withdrawn from the vessel to leave the deployed stent in position within the vessel. The amnion tissue described herein provides several advantages. With respect to delivery of the stent, the amnion tissue has the advantage that the tissue can stretch generally without rupturing or cracking even with a reasonably large amount of stretching. Thus, tissue modified stents can generally be deployed similarly to the unmodified stent.

The Structure of the Biocompatible Stent

In some embodiments, the amnion tissue can be rolled into a tube as covering or lining for stent scaffold. As shown in FIG. 2A, a sheet of amnion tissue 101 is rolled into a tube 102 with side and cross sectional views of the tube showing a butt seam 103. The amniotic tissue separated from the amniotic sac is about 0.002 inch thick. This layer thickness allows more than one layer of amnion tissue to be used and still meet appropriate thicknesses for in vivo application. The multilayer configuration of a covering and/or lining may be advantageous in some applications because the increased thickness of overall amnion tissue provides increased tissue strength and easier manipulation. In some embodiments, a covering and/or lining can comprise one to twenty five layers, in further embodiments from about 2 to about fifteen and in additional embodiments from about 2 to about 10 layers. If multiple layers of tissue are used, some of the layers can comprise tissue derived from other sources as long as at least one layer is amnion tissue, although it may be desirable to use amnion tissue for all of the tissue layers. Other types of tissue are described below. In some embodiments, the amnion tissue can be placed at one surface of the stack of layers, and in further embodiments, amnion tissue can be placed at both surfaces of the stack of layers. In some embodiments, the average tissue thickness of a lining, a covering or combination thereof can be from about 0.001 to about 0.05 inches, in further embodiments from about 0.002 to about 0.03 inches, and in additional embodiments from about 0.002 to about 0.02 inches thick. For example as shown in FIG. 2(b), a long amnion membrane 104 can be rolled into a tube 105 with multiple layers of the amnion tissue having a butt seam 106. The layers may be fastened together by gluing, suturing, or mechanical means of attachment. A person of ordinary skill in the art will recognize that additional ranges of layer numbers and thicknesses within the explicit ranges above are contemplated and are within the present disclosure.

The amnion tissue used can be ablated with a laser or cut mechanically with a hold punch or other appropriate tool to create holes on the tissue. The holes may have any suitable shape or size, such as ranging from about 5 microns to about 1000 microns in average diameter and in further embodiments from about 10 microns to about 500 microns in average diameter. A person of ordinary skill in the art will recognize that additional ranges of average diameter within the explicit ranges above are contemplated and are within the present disclosure. When used as covering or lining on a stent scaffold, the presence of the holes on the amnion tissue can allow increased vessel tissue in-growth and therefore expedite colonization by native cells. Additionally, drugs such as heparin, paclitaxel, rapamycin, or other suitable drugs can be loaded inside the holes of the amnion tissue to be released inside the vessel for desired therapeutic uses. In some embodiments, the amnion tissue can be non-cryopreserved at a temperature of −60 to −100° C. when used to cover or line the stent scaffold. In other embodiments, the amnion membrane can be cryo preserved before being used to cover or line the stent scaffold. While cryopreservation can be used for preserving cell cultures for some cell types and has been proposed for tissue storage, cryopreservation can change the mechanical properties of the tissue in undesirable ways, for example, with the loss of at least some of the elasticity. For tissues with viable cells, cryopreservation can lead to cell death. Therefore, in some embodiments, it an be desirable to store the tissue at temperatures above −55° C., in further embodiments greater than about −30° C. and in other embodiments from about −20 to about 10° C. Some specific storage techniques for tissue with viable cells are described further below. A person of ordinary skill in the art will recognize that additional ranges of storage temperature within the explicit ranges above are contemplated and are within the present disclosure.

Alternatively, amnion suture, filaments, or yarns known in the art can be used to make an amnion fabric 108 as shown in FIG. 2C. The amnion fabric can then be used to form the covering or linings for stent scaffold similarly as the amnion tissue. One or more layers of amnion fabric can be used to achieve overall desired thicknesses as described above.

Figures 3A, 3B, 3C, 3D:
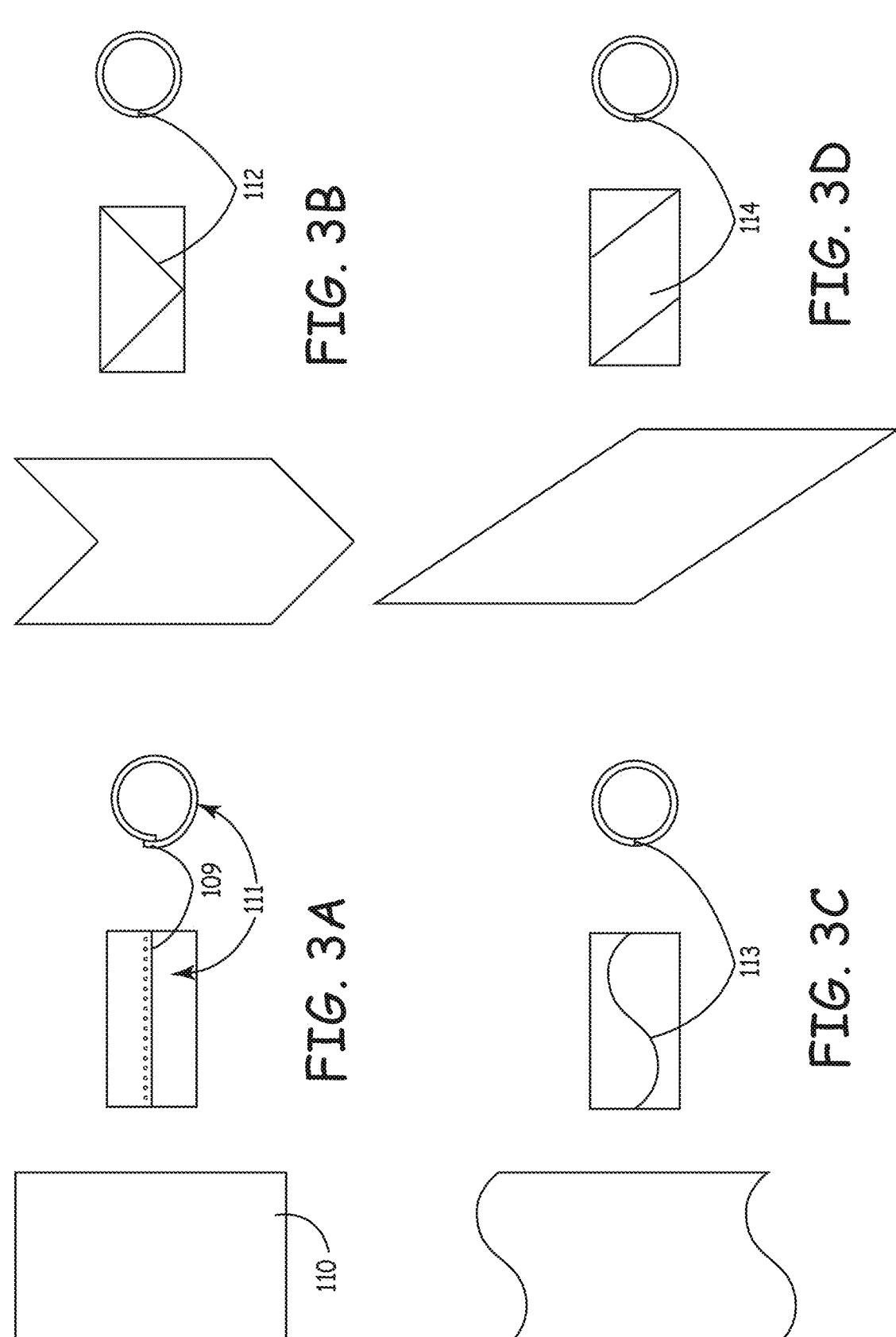
FIG. 3A is a set of drawings showing a sheet of amnion being rolled into a tube with side and cross-sectional views of the tube showing a lap seam.
FIG. 3B is a set of drawings showing an amnion sheet with a V seam being formed into a tube with side and cross-sectional views of the tube showing a butt joint.
FIG. 3C is a set of drawings showing an amnion sheet with a sinusoidal seam being formed into a tube with side and cross-sectional views of the tube showing a butt joint.
FIG. 3D is a set of drawings showing an amnion sheet with a circumferential helical seam being formed into a tube with side and cross-sectional views of the tube showing a butt joint.
Figures 4A, 4B, 4C, 4D:
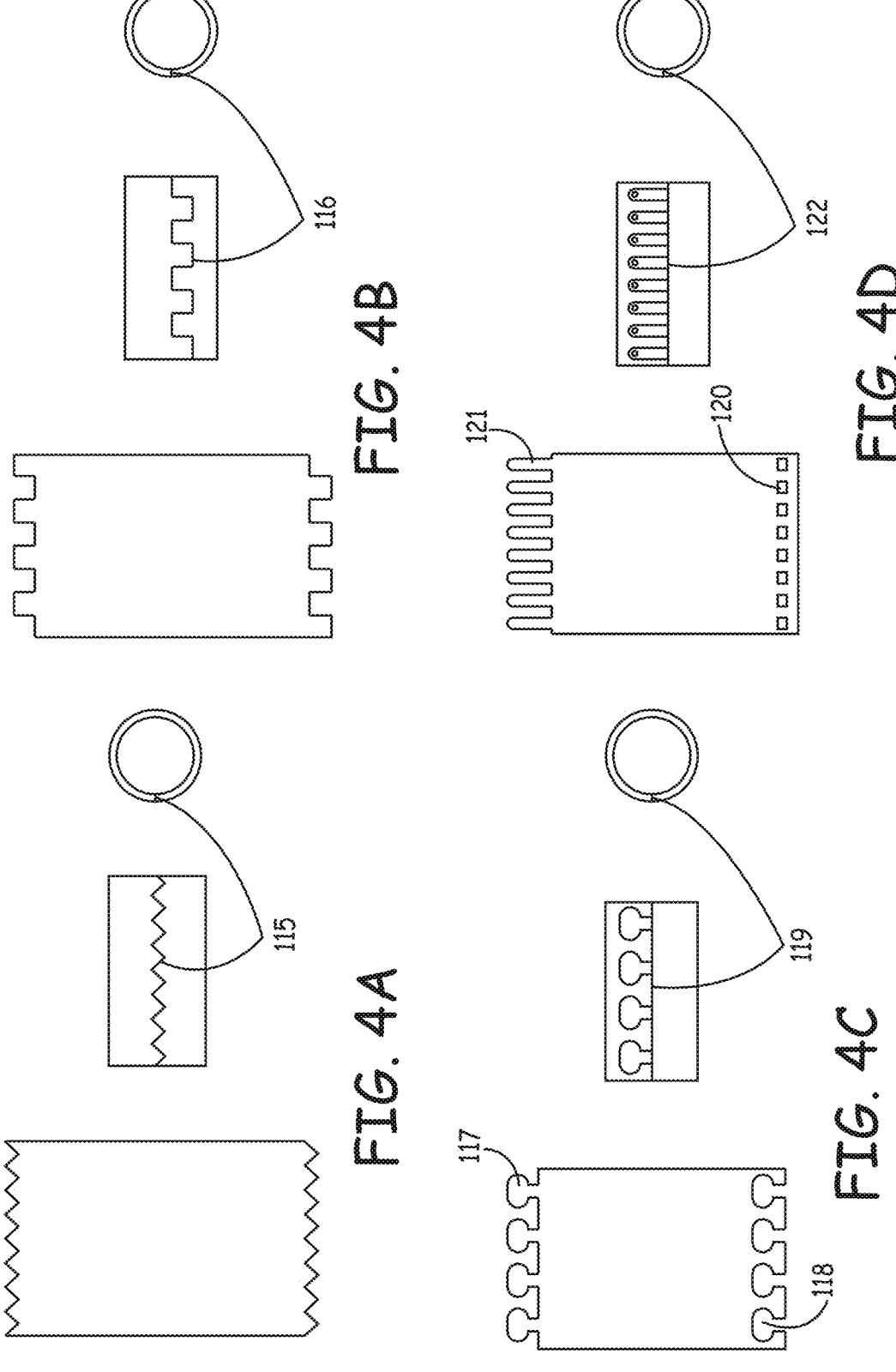
FIG. 4A is a set of drawings showing an amnion sheet with a saw tooth seam being formed into a tube with a butt joint.
FIG. 4B is a set of drawings showing an amnion sheet with a square notched seam being formed into a tube with a butt joint.
FIG. 4C is a set of drawings showing an amnion sheet with a male and female interlocking joints being formed into a tube with a butt joint.
FIG. 4D is a set of drawings showing an amnion sheet with a series of belts and slots being formed into tube with a butt joint.

Seams, such as longitudinal seams, of the amnion membrane tube, cuff or other tissue structure can be joined via mechanical, electronic, adhesive, energy based method, or a combination thereof such as sewing, gluing, clipping, stapling, riveting, ultrasonic welding, laser welding, thermal bonding, pressure fit, interlocking with stent scaffold, or a combination thereof. For example, these procedures can be performed with suitable medical devices. For example, sewing can be performed with suture, gluing can be performed with surgical adhesives, stapling and clipping can be performed with surgical staples and clips. The seam may be a butt seam as shown in FIG. 2A or a lap seam as shown in FIG. 3A. Referring to FIG. 3A, amnion tissue 110 is rolled into a tube 111, with side and cross sectional views of the tube showing a lap seam 109. The seam can have a variety of configurations. For instance, the seam can be a V seam 112, a sinusoidal seam 113, or a circumferential helical seam 114 as shown in FIGS. 3B, 3C, and 3D respectively. Alternatively, the seam can be a saw tooth seam 115, a square notched seam 116, a seam 119 with male tab 117 and female tab 118 interlocking each other, or a seam 122 with a series of jointed belts 121 and slots 120 as shown in FIGS. 4A, 4B, 4C, and 4D, respectively. Although the seams shown in FIGS. 3B-3D and 4A-4D are butt seams, lap seam configuration can be similarly applied to these alternative seam options.

Figures 5A, 5B:
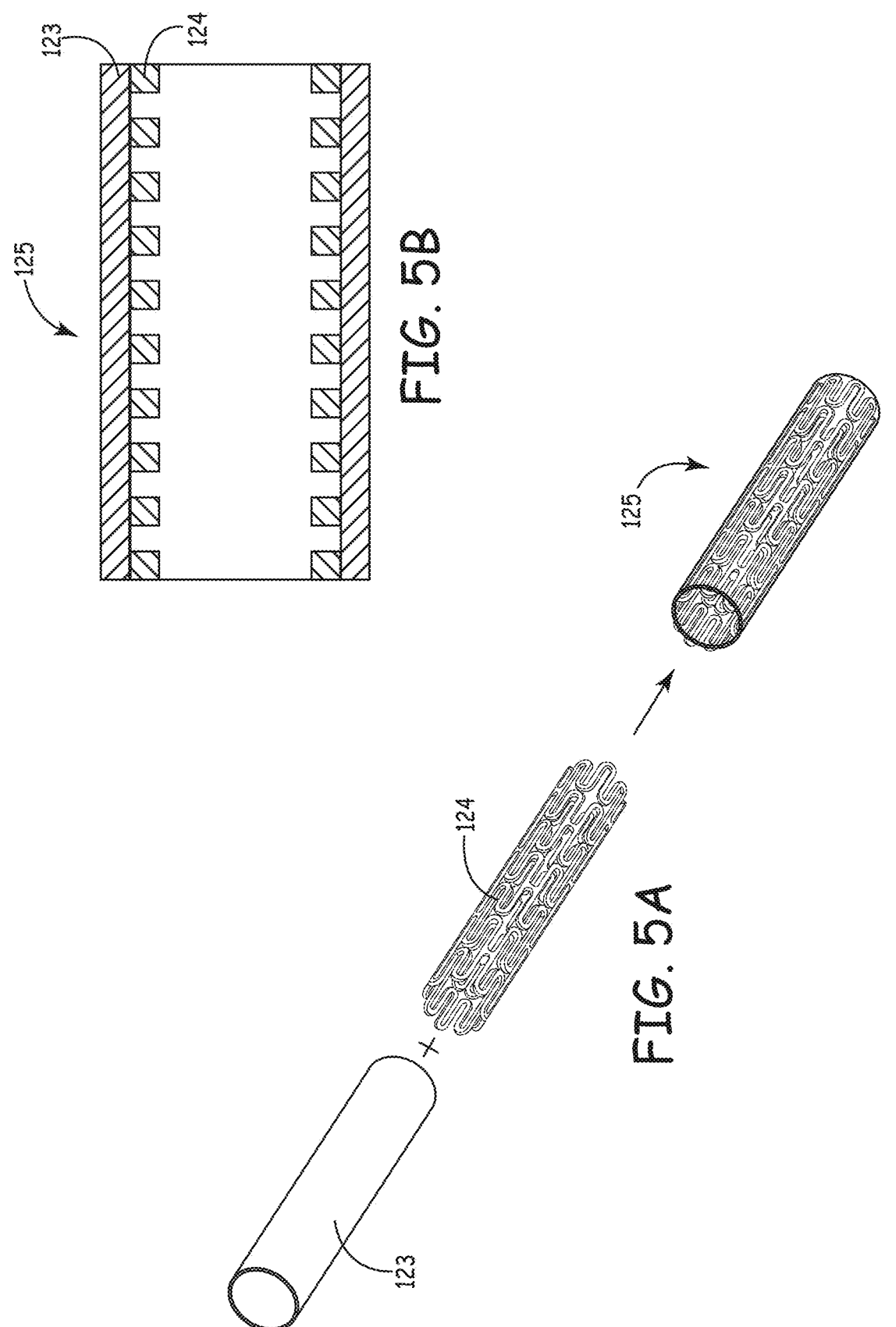
FIG. 5A is a set of drawings showing an amnion membrane tube being combined with an expandable stent scaffold to form a biocompatible stent.
FIG. 5B is a longitudinal cross-sectional view of the biocompatible stent of FIG. 5A.
Figures 6A, 6B, 6C, 6D, 6E:
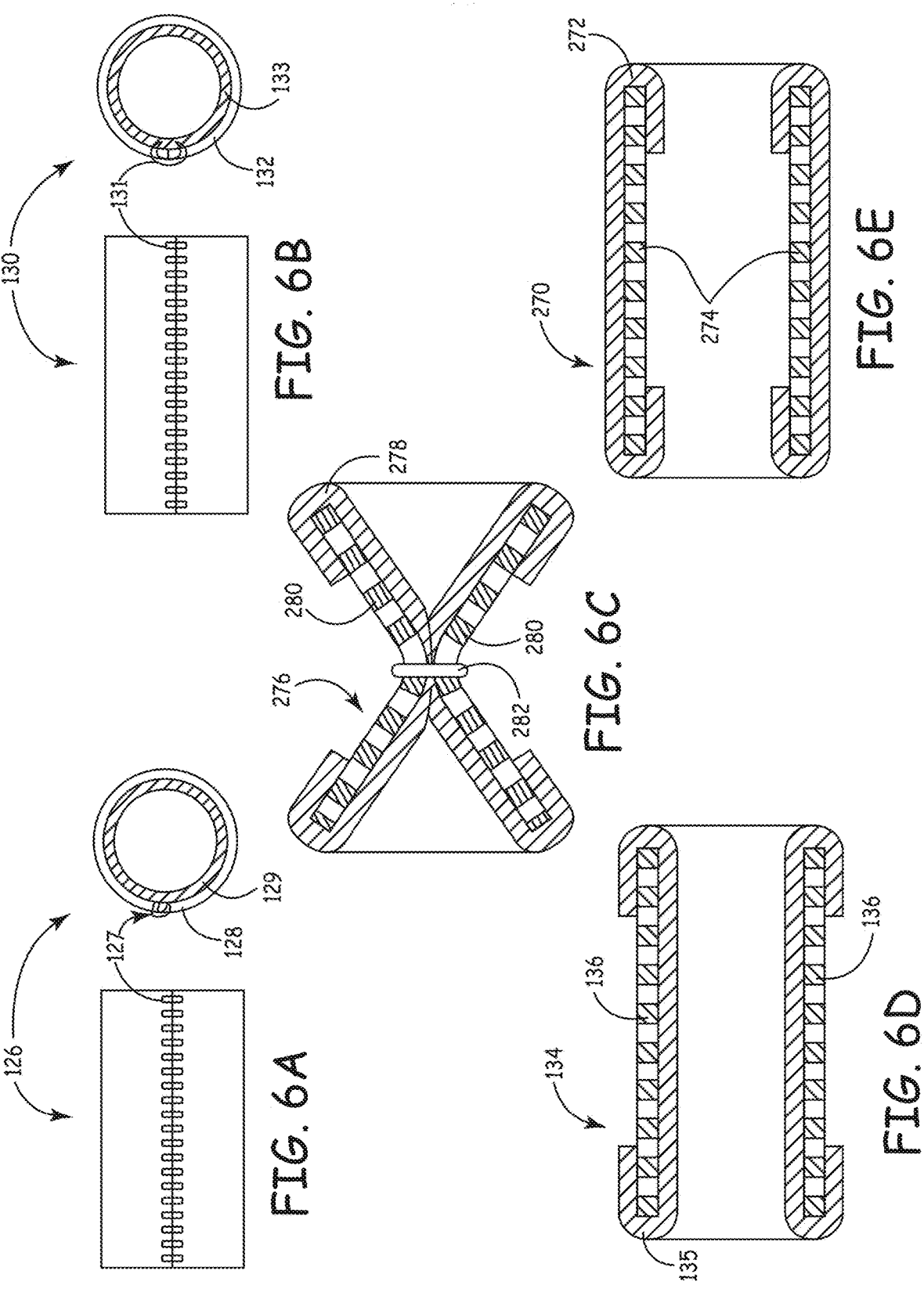
FIG. 6A is a side view and a sectional view of a biocompatible stent with fish hook liker barbs securing the amnion covering to the stent scaffold.
FIG. 6B is a side view and a sectional view of a biocompatible stent with staples securing the amnion covering to the stent scaffold.
FIG. 6C is a longitudinal cross-sectional view of a biocompatible stent with an inner sleeve with rolled over ends on a stent scaffold being crimped in the middle.
FIG. 6D is a longitudinal cross-sectional view of a biocompatible stent with an inner sleeve with rolled over ends on a stent scaffold.
FIG. 6E is a longitudinal cross-sectional view of a biocompatible stent with an outer lining with rolled over ends on a stent scaffold.

The amnion tissue can be attached to a stent scaffold in a variety of ways. Referring to FIG. 5A, an amnion tube 123 is slid over a stent scaffold 124 to form an amnion tissue covered stent 125. FIG. 5B is a longitudinal cross-sectional enlarged view of the stent 125 with the amnion layer 123 covering the stent scaffold mesh 124. The covering or lining maybe attached to the stent with mechanical fixation means, such as suture, staples, hooks, rivets or combinations thereof. The covering or lining may also be adhesive bonded to the stent. For example, FIGS. 6A, 6B, 6D, and 6E show several ways amnion covering or lining is attached to the stent scaffold. Referring to FIG. 6A, a biocompatible stent 126 comprises fish hook like barbs 127 to secure layers of amnion covering 128 to stent scaffold 129. Referring to FIG. 6B, a biocompatible stent 130 comprises staples 131 to secure layers of amnion covering 132 to stent scaffold 133. FIG. 6D is a longitudinal cross-sectional enlarged view of biocompatible stent 134 lined with an amnion membrane 135 by rolling the amnion tissue over the ends on the stent scaffold 136. FIG. 6E is a longitudinal cross-sectional enlarged view of biocompatible stent 270 lined with an amnion membrane 272 by rolling the amnion tissue over the ends of the stent scaffold 274. Similar ways of forming the tissue structure can be adapted for embodiments of the stent in which the stent is crimped or otherwise constrained to form a partially or totally occlusive structure. Referring to FIG. 6C, a biocompatible stent 276 with inner amnion tissue lining 278 rolled over the ends of the stent scaffold 280 is crimped in the middle with crimp 282. Depending on the desired shape and function, the stent scaffold could be lined or covered and crimped differently.

Figure 7A:
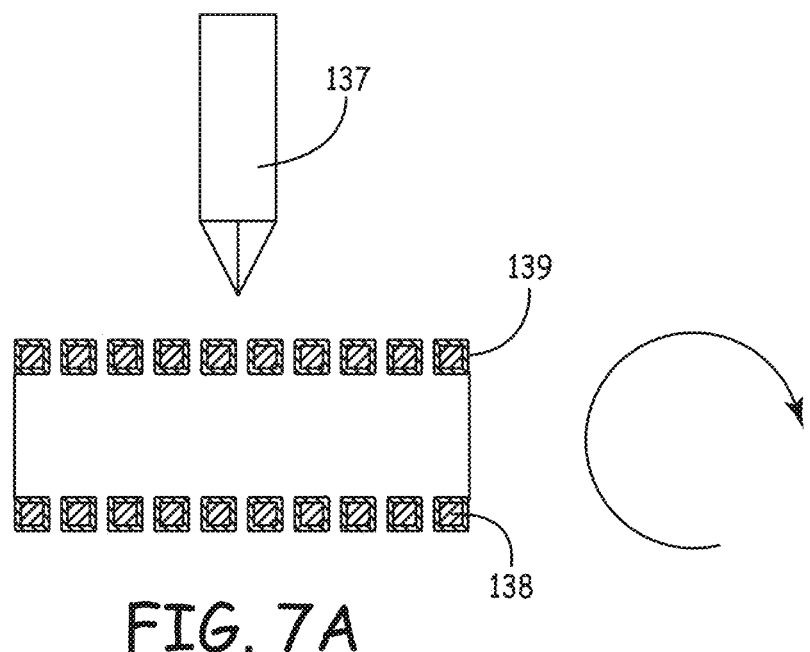
FIG. 7A is a schematic side view of a nozzle spraying an amnion solution to a stent scaffold while the stent scaffold is rotating to encapsulate the mesh of the stent scaffold into the amnion solution.
Figure 7B:
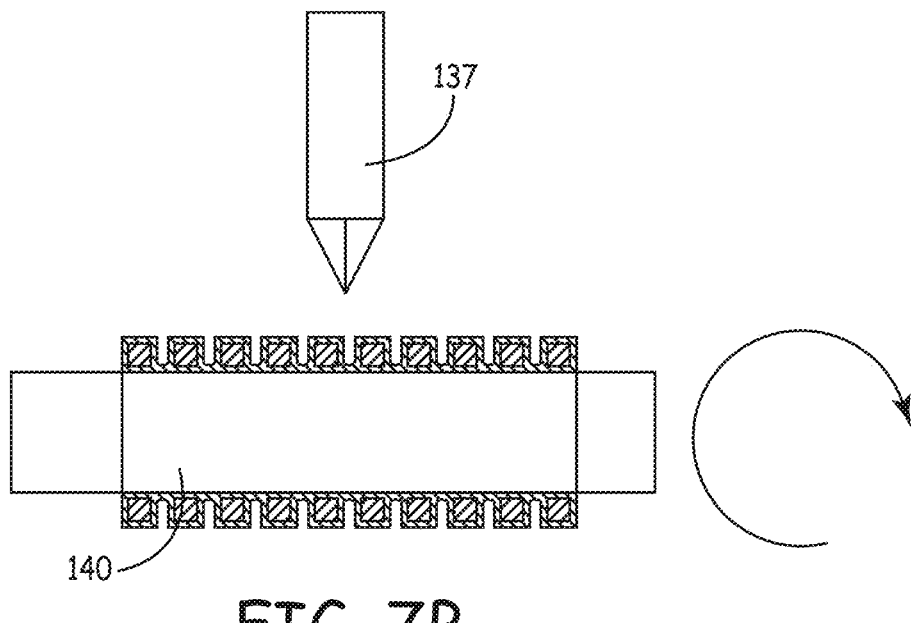
FIG. 7B is a schematic side view of the stent scaffold on a mandrel while being sprayed.

The amnion tissue may also be digested using chemical, enzymatic, or mechanical means to form an amnion solution. Stent scaffold can be coated with the amnion tissue solution through spray coating, dip coating or electrophoretic means. The amnion coating may be smooth or provide a corrugated surface on the surface of the stent scaffold. Referring to FIG. 7A, a nozzle 137 is used to spray a liquid solution of amnion on a stent scaffold 138 while the stent scaffold is rotating. The mesh of the stent scaffold 138 is shown to be coated with an amnion coating 139. As shown in FIG. 7B, a rotating mandrel 140 is used to support the stent scaffold while being spayed. Alternatively, the stent scaffold may be dip coated by dipping the stent scaffold into a solution of amnion before being dried to form the amnion coating. The stent scaffold may already have been covered with amnion covering or lining before being additionally covered with amnion coating. The amnion solution may also be used as adhesive to secure amnion membrane to the stent scaffold.

FIGS. 8-11 discloses a variety ways of modifying the stent scaffold with amnion tissue using a combination of materials. Referring to FIG. 8A, a longitudinal cross-sectional enlarged view of a stent 141 shows stent scaffold mesh 143 is lined with amnion layer 142. FIG. 8B shows a longitudinal cross-sectional enlarged view of a stent 144 with stent scaffold mesh 145 being lined with two amnion layers 146. FIG. 8C shows a longitudinal cross-sectional enlarged view of a stent 147 with stent scaffold mesh 148 being sandwiched between two amnion layers 149. FIG. 8D shows a longitudinal cross-sectional enlarged view of a stent 150 with amnion layer 151 being sandwiched between two stent scaffold meshes 152. In some embodiments, the stent scaffold is completely encapsulated with a biocompatible material. For example, FIG. 9A shows a longitudinal cross section of a biocompatible stent 153 with an exterior amnion covering 154 which is encapsulated through the stent scaffold mesh 155 to provide for a smooth inner and outer surface. FIG. 9B shows a longitudinal cross section of a biocompatible stent 156 with an interior amnion covering 157 which is encapsulated through the stent scaffold mesh 158 to provide for a smooth inner and outer surface. FIG. 9C shows a longitudinal cross section of stent 159 with a stent mesh 162 sandwiched between an interior amnion lining 160 and an exterior amnion covering 161, both 160 and 161 are encapsulated through the stent mesh 162. FIG. 9D shows a longitudinal cross section of stent 163 with amnion membrane 164 sandwiched between two coaxial stents 165 and 166, with the amnion membrane 164 encapsulated through the stent meshes 165 and 166.

Figures 10A, 10B, 10C:
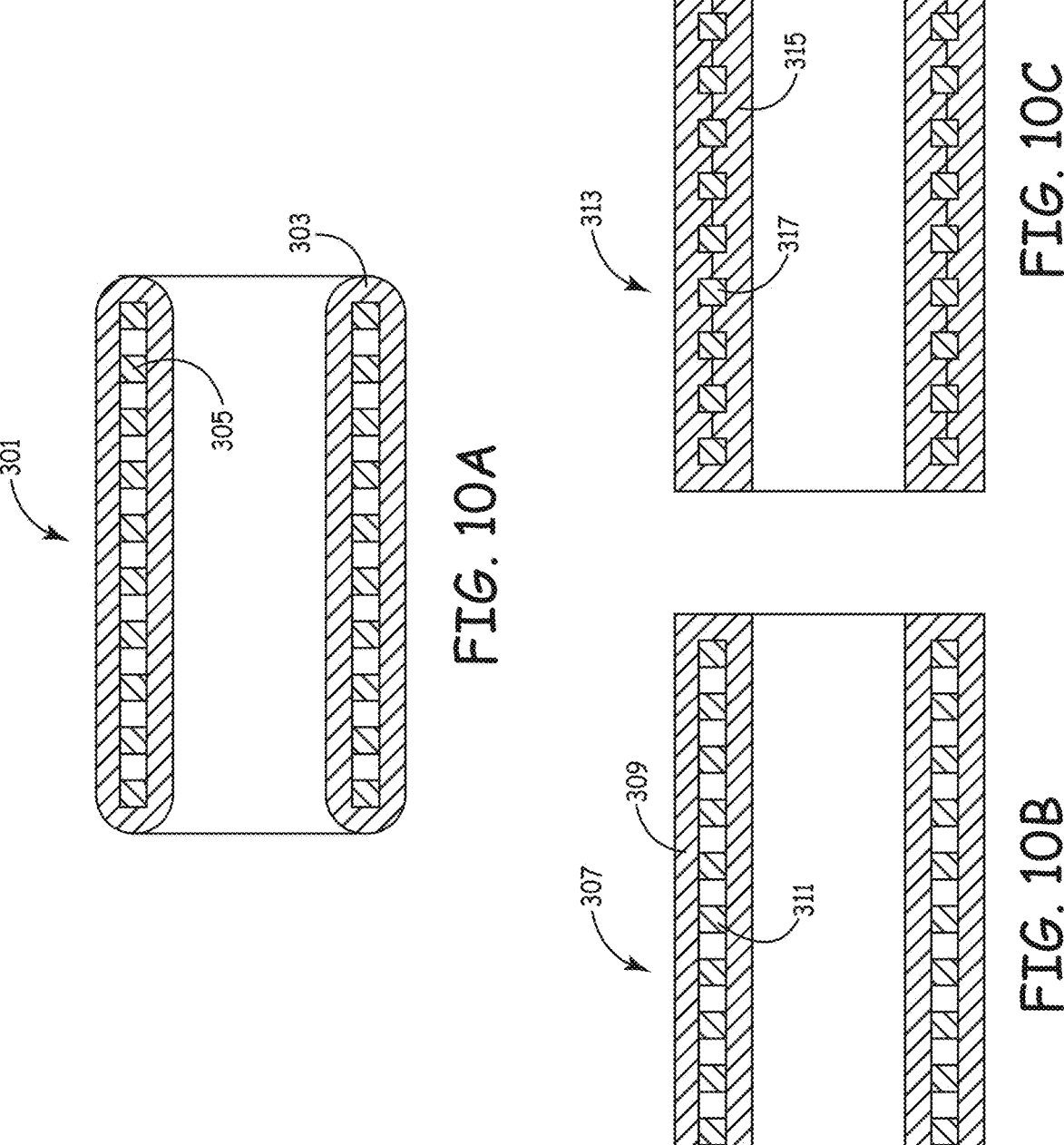
FIG. 10A is a cross sectional view showing the longitudinal cross section of biocompatible stents with the amnion tissue encapsulating the stent scaffold to form inner and outer coatings with wrapped around end section.
FIG. 10B is a cross sectional view showing the longitudinal cross section of biocompatible stents with the amnion tissue encapsulating the stent scaffold to form inner and outer coatings with coated end section.
FIG. 10C is a cross sectional view showing the longitudinal cross section of biocompatible stents with the amnion tissue encapsulating the stent scaffold to form inner and outer coatings with coated end section and with amnion tissue encapsulating through the stent mesh.

There are a variety ways to encapsulate a stent scaffold into amnion tissue such as those illustrated in FIGS. 10A-C. Specifically, FIG. 10A shows a longitudinal cross sectional view of biocompatible stent 301 with the amnion tissue 303 encapsulating the stent scaffold 305 to form inner and outer coatings of amnion tissue with wrapped around end section. FIG. 10B shows a longitudinal cross sectional view of biocompatible stent 307 with the amnion tissue 309 encapsulating the stent scaffold 311 to form inner and outer coatings of amnion tissue with coated end section. FIG. 10C shows a longitudinal cross sectional view of biocompatible stent 313 with the amnion tissue 315 encapsulating the stent scaffold 317 to form inner and outer coatings of amnion tissue with coated end section and with amnion tissue encapsulating through the stent mesh.

Figures 8A, 8B, 8C, 8D:
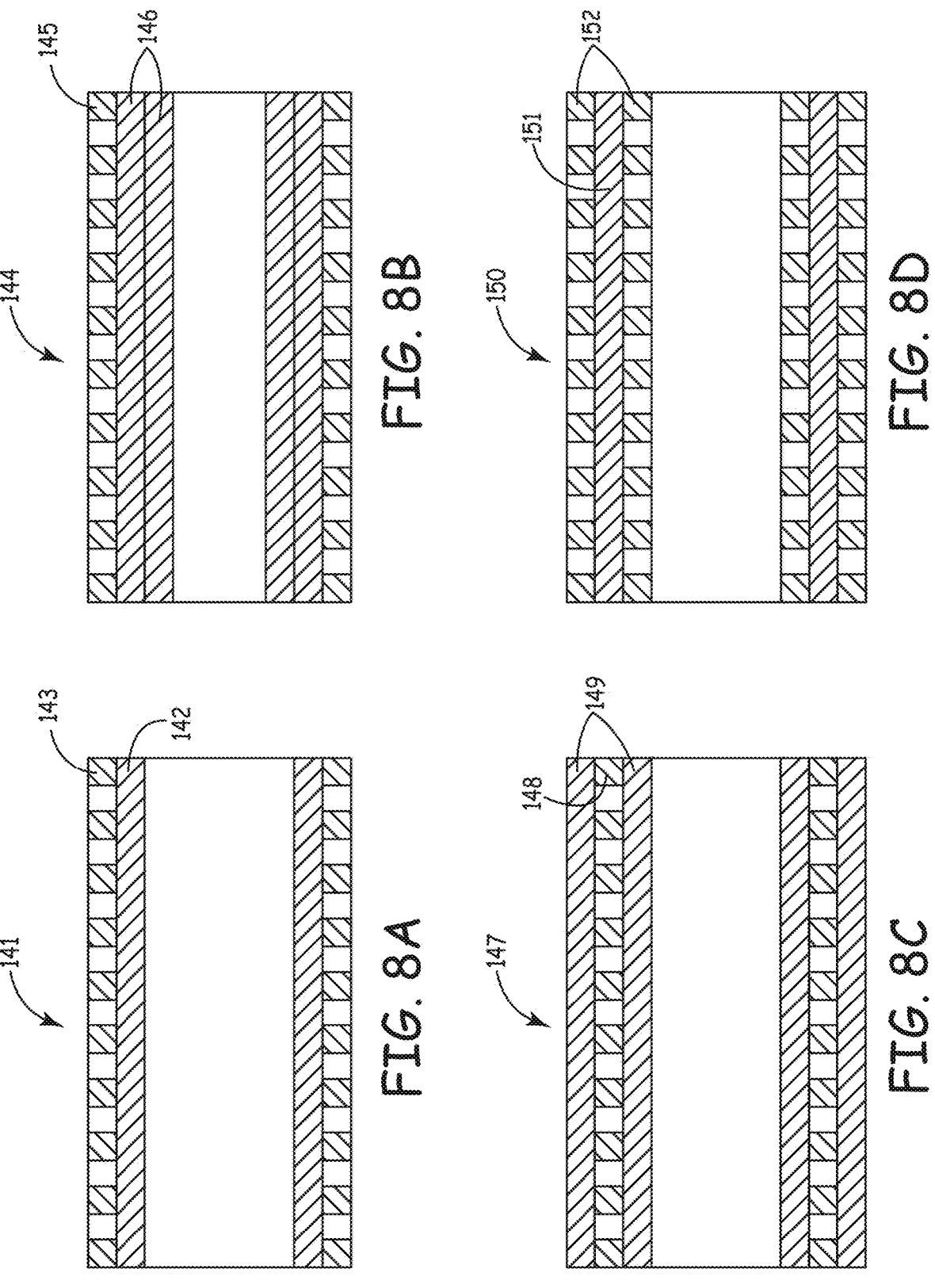
FIG. 8A is a cross sectional view showing the longitudinal cross section of biocompatible stents with an inner amnion sleeve.
FIG. 8B is a cross sectional view showing the longitudinal cross section of biocompatible stents with two inner sleeves.
FIG. 8C is a cross sectional view showing the longitudinal cross section of biocompatible stents with an inner and an outer amnion sleeves.
FIG. 8D is a cross sectional view showing the longitudinal cross section of biocompatible stents with an amnion layer sandwiched between two coaxial stent scaffolds.
Figures 9A, 9B, 9C, 9D:
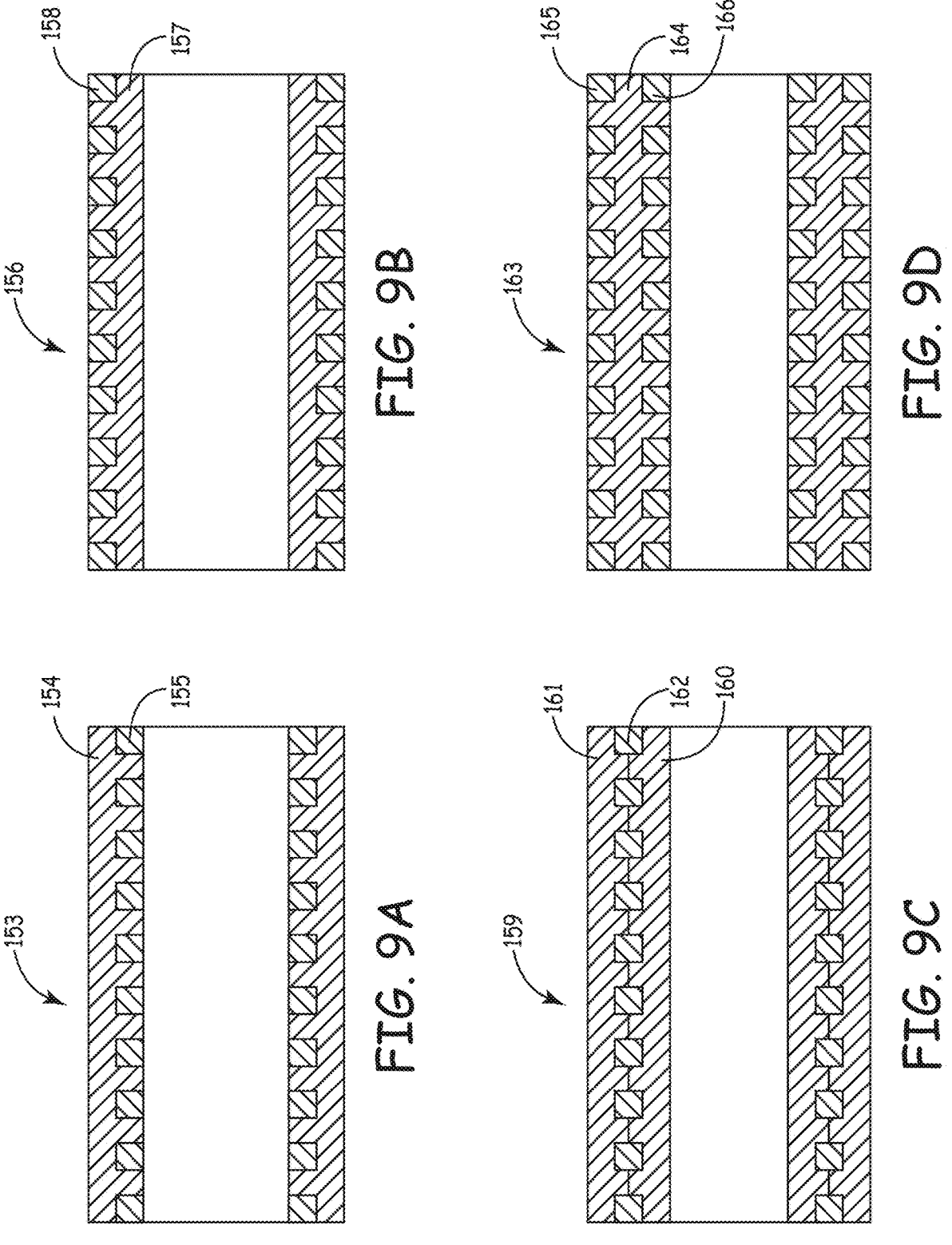
FIG. 9A is a cross sectional view showing the longitudinal cross section of biocompatible stents with the amnion tissue encapsulating through the stent scaffold mesh to form an outer coating.
FIG. 9B is a cross sectional view showing the longitudinal cross section of biocompatible stents with the amnion tissue encapsulating through the stent scaffold mesh to form an inner coating.
FIG. 9C is a cross sectional view showing the longitudinal cross section of biocompatible stents with the amnion tissue encapsulating through the stent scaffold mesh to form inner and outer coatings.
FIG. 9D is a cross sectional view showing the longitudinal cross section of biocompatible stents with the amnion tissue encapsulating through the stent scaffold mesh to form an amnion filling to fill the gaps between two coaxial stent scaffolds.

The double coaxial stent scaffold configuration displayed in FIGS. 8D and 9D may have special technical advantage. For instance, the double coaxial stent can provide a stronger support to the vessel where it is deployed, and the stents themselves can hold the amnion tissue in place without additional anchoring, although additional anchoring can be used if desired. Other alternative stent configurations can also be used to achieve desired properties. For example, FIG. 11A shows a longitudinal view of an amnion graft 167 comprises an amnion covering 170 covering at left and right ends of stent scaffolds 168 and 169 respectively. The center portion of the covering 170 is unsupported by stent scaffold. FIG. 11B shows a longitudinal cross section of a bifurcated biocompatible stent 171 comprises a bifurcated stent scaffold mesh 172 being covered with amnion tissue 173. FIG. 11C shows a longitudinal view of an amnion graft 174 comprises a stent scaffold 175 with both ends of the scaffold being covered with amnion tissue sections 176 and 177 respectively and the center portion of the stent scaffold not covered that allows for perfusion through the central portion of the stent i.e. to a branch vessel. Alternatively, to fulfill branching perfusion needs, a side hole 178 may be cut into an amnion tissue 179 as shown in FIG. 11D. When the amnion tissue 179 is rolled into a tube 180, a branching hole 181 is created to allow perfusion flow through the branching hole. The embodiments in FIGS. 11A-E as well as other embodiments described herein can be adapted with tissue cuffs and additional tissue layers such that the stent scaffold is fully covered with amnion tissue.

Figures 17A, 17B, 17C:
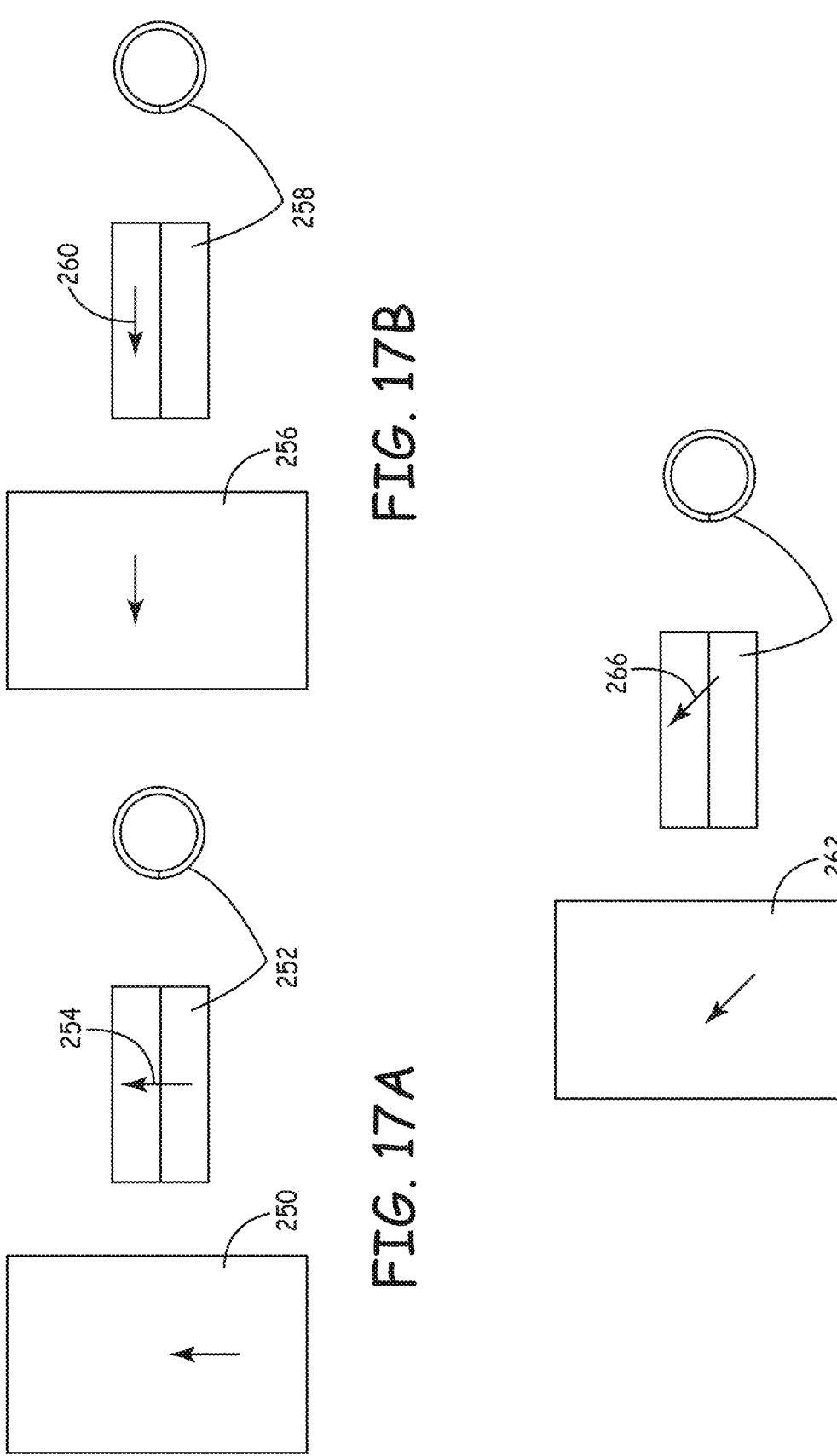
FIG. 17A is a set of drawings showing a sheet of amnion being rolled into a tube with side and cross-sectional views of the tube showing the predominant fiber orientation in the circumferential direction.
FIG. 17B is a set of drawings showing a sheet of amnion being rolled into a tube with side and cross-sectional views of the tube showing the predominant fiber orientation in the longitudinal direction.
FIG. 17C is a set of drawings showing a sheet of amnion being rolled into a tube with side and cross-sectional views of the tube showing the predominant fiber orientation at an angle in the longitudinal direction.

The stretching ability of the amnion tissue is largely attributed to the collagen content in the tissue. The stretch ability of the collagen is known to be predominantly unidirectional. The direction of the stretch ability of the amnion tissue can be therefore adjusted based on different stent scaffold properties and application needs. In one embodiment, the stretch ability of the amnion tissue can be oriented in the circumferential direction of stent scaffold. In another embodiment, the stretch ability of the amnion tissue can be oriented in the longitudinal direction of the stent scaffold. In yet another embodiment, the stretch ability of the amnion tissue can be oriented at an angle to the longitudinal direction of the stent scaffold. In some embodiments the amnion tissue may be better accommodated if the amnion sheet is associated with the stent on a "bias" when a piece of amnion sheet has stretch direction that is on a bias with respect to the edges of sheet. In one embodiment, the bias is 45 degree. Referring to FIG. 17A, a set of drawings shows a sheet of amnion 250 being rolled into a tube 252 with side and cross-sectional views of the tube showing the predominate fiber orientation in the circumferential direction 254. FIG. 17B shows a set of drawings of a sheet of amnion 256 being rolled into a tube 258 with side and cross-sectional views of the tube showing the predominate fiber orientation in the longitudinal direction 260. FIG. 17C is a set of drawings showing a sheet of amnion 262 being rolled into a tube 264 with side and cross-sectional views of the tube showing the predominate fiber orientation 266 at an angle to the in the longitudinal direction.

Biocompatible Material

A variety of biocompatible materials can be used to modify stent scaffold. For instance, naturally derived biocompatible materials include, for example, amnion tissue, collagen type I-VI, small intestinal submucosa tissue, pericardium tissue, placental tissue, placenta veins or arteries from mammal sources or combinations thereof. In particular, amnion tissue can be particularly desirable due to the natural very low presentation of antigens associated with this tissue as well as the expandable nature of this tissue while generally avoiding mechanical damage. Synthetic biocompatible material can be used in addition to naturally derived compatible materials including, for example, silicone, polyether block amide (PEBAX), polyurethane, silicone polyurethane copolymer, nylon, polyethylene terephthalate (PET), Gore-Tex™ (polytetrafluoroethylene, or ePTFE), Kevlar™ (para aramide), ultra high molecular weight polyethylene such as Spectra™, and Dyneena™, polyvinyl chloride (PVC) or combinations thereof.

Amnion Tissue

The amniotic sac of the placenta tissue is composed of two layers of tissue, the chorion and the amnion, with the amnion tissue being the inner most layer of the amniotic sac. As shown in FIG. 1, the amnion tissue is composed of a single epithelial layer, a thick basement membrane, and an avascular stroma. The amnion layer is known to have good elasticity and low immunogenicity making it a desirable naturally derived biocompatible material. Low risk of immunogenicity is an important property of embodiments of the biocompatible stents described herein. The amnion tissue is also desirable since it can provide a good surface for colonization by native cells, such as endothelial cells that make up the surface of blood vessels and/or fibroblast that occupy the vessel matrix below the endothelial cells. Placental tissue can similarly be used, for example, with the amnion component positioned for exposure to the native tissues. The placental tissue can provide a greater thickness while providing the amnion tissue surface, if desired.

Class I Human leukocyte antigen (HLA), -A, -B, and -C induce specific immune responses by presenting peptide antigens to T cells. Because random transplantation between donor and host is unlikely to result in a matching of HLA-A, B or C antigens, the mismatch is the primary cause of transplant rejection. The HLA-A, -B, and -C genes are down regulated in amnion tissue. In contrast. HLA-G is expressed in amnion tissue. HLA-G is thought to be involved in the induction of immune tolerance by acting as ligand for inhibitory receptors present on NK cells and macrophages. Additionally, amnion epithelia cells (AECs) also do not express HLA-A, -B, -D, and -DR antigens on the cell surface, but express HLA-G on their surfaces. Amnion tissue including AECs therefore has low immunogenicity.

The amnion layer of the amniotic sac can be separated from the chorion and used alone or alternatively both the amnion or chorion layers can be used together as material to modify stent scaffold. The chorion and the amnion layers of the amniotic sac are not strongly connected and therefore can be separated by mechanical methods such as blunt dissection or the like. The separated amnion layer can be used directly (fresh) or can be reconstituted before being used to modify stent scaffold. Placental tissue can be obtained from birthing centers, such as hospitals. The placenta is generally discarded, and the placenta can be harvested for use. The placenta can be appropriately stored and transported for processing into the tissues described herein. In particular, the tissue can be appropriately hydrated and refrigerated for transport under reasonably sterile conditions. Appropriate tissue handling procedures are known in the art and can be adapted for the purposes described herein.

The epithelium layer of the amnion tissue may be removed or left intact. The amniotic tissue may be chemically modified, treated with radiation, or treated with heat. For example, the amnion tissue can be treated with infrared radiation to warm the tissue gently or with ultraviolet radiation under gentle conditions to sterilize the surface of the tissue. The most common chemical modification comprises crosslinking or partially crosslinking amnion tissue. Crosslinking of the tissue can provide mechanical stabilization of the material. However, crosslinking may be harmful to any viable cells in the treated tissue. Crosslinking agents such as glutaraldehyde, triglycidylamine, or EDC (1-Ethyl-3-[3-dimethylaminopropyl] carbodiimide Hydrochloride) can be used. Glutaraldehyde has been used extensively in the formation of bioprosthetic tissues for implantation into humans. In vitro crosslinking/stabilization of bioprosthetic tissue with polyamines along with coupling agents and/or coupling enhancers is described further in published U.S. patent application 2006/0159641A to Girardot et al., entitled "Variably Crosslinked Tissue," incorporated herein by reference. Additionally, genipin has been used in vascular stent as a collagen crosslinking/stabilization agent for treating vulnerable plaques of a patient as described in U.S. Pat. No. 7,351,421 to Sung et al., entitled Drug-Eluting Stent Having Collagen Drug Carrier Chemically Treated with Genipin," incorporated herein by reference. The properties of triglycidylamine (TGA) crosslinked tissue are described further in Van Wachem P B, Brouwer L A, Zeeman R, et al. *J Biomed Mater Res* 2000; 53(1): 18-27 and Connolly J M, Alferiev I, Clark-Gruel J N, et al. *Am J Pathol* 2005; 166(1): 1-13), both of which are incorporated herein by reference.

The amnion tissue can be used with viable cells or without viable cells. The stem cells present in the amnion tissue may assist with the growth of endothelial cells on inner lumen of the biocompatible stent. For example, when delivering the biocompatible stent to the implant location it may be desirable to condition or injure the implant location prior to stent implantation or concurrent with stent implantation. The injury to the native tissue should provide for faster incorporation or healing of the amnion tissue. The degree of crosslinking of the amnion tissue can be used to control the absorption rate of the amnion tissue. Non-crosslinked tissue will absorb faster. The amnion tissue may be seeded with additional stem cells if desired.

Suture, filaments, or yarns may be derived from amnion tissue and be used to construct amnion fabric by weaving, braiding, or knitting of amnion suture, filaments, or yarns. In some embodiments, amnion tissue can be mechanically formed into filaments, yarn or the like, for example, by cutting thin strips of tissue. The filaments or yarn can then be fabricated into the fabric or the like. The amnion fabric can be manufactured into desired thickness, strength, stretch ability, and permeability based on application needs. Other materials such as biocompatible polymer and metal may be used in conjunction with the amnion suture, filaments, or yarns to construct the fabric to achieve desired properties.

The top layer of amnion tissue generally comprises a single layer of amnion epithelial cells (AEC). AEC is reported to have stem cell like characteristics without the need of a feeder layer as disclosed by Niknejad et al. in "Properties of the amniotic membrane for potential use in tissue engineering", European Cells and Materials Vol. 15, 2008, pages 88-99, incorporated herein by reference. According to Niknejad, the AEC can be isolated for separate use or can be removed from intact amnion tissue to form denuded amnion tissue. In some embodiments, the amnion tissue used can contain AECs. In other embodiments, the AECs are removed from the amnion tissue and the denuded amnion tissue is used. In further embodiments, AECs are used with all or a portion of the collagenous section of the amnion removed to form the amnion tissue.

Solubilized Amnion Tissue

Amnion tissue can also be solubilized using chemical, enzymatic, mechanical, or a combination of means to form an amnion solution. Voytik-Harbin et al. for example has disclosed in U.S. Pat. No. 7,147,871 incorporated herein by reference, an enzymatic digestion protocol to digest intestinal submucosa. Similar enzymatic digestion can be used to form amnion solution also. Isolated amnion tissue is typically rinsed extensively with a hypotonic solution to lyse any cells still associated with the amnion tissue and to eliminate cell degradation products. To produce the solubilized forms of amnion, the amnion tissue is treated with a disruptive agent that solubilizes the amnion tissue without substantial destruction of the collagen components of the amnion tissue. In one embodiment the amnion tissue is treated with one or more enzymes for a predetermined length of time sufficient to hydrolyze at least a portion of the amnion tissue structural components and produce an amnion hydrolysate. The amnion tissue can be comminuted before enzymatic digestion of the amnion by tearing, cutting, grinding, or shearing the harvested amnion tissue. More particularly, the amnion tissue can be comminuted by shearing in a high speed blender, or by grinding the amnion tissue in a frozen or freeze-dried state, and then lyophilizing the material to produce a powder having particles ranging in size from about 0.1 to about 1.0 mm$^2$. The amnion powder can thereafter be hydrated with water or buffered saline to form an amino fluid of liquid or paste-like consistency. In one embodiment the amnion tissue is comminuted by freezing and pulverizing the amnion tissue under liquid nitrogen in an industrial blender. In some embodiments, the comminuted or pulverized amnion tissue can be used directly without further treatment to modify stent scaffolds. Preparation of fluidized forms of intestinal submucosa tissue is described further in U.S. Pat. No. 5,275,826, to Badylak et al., entitled "Fluidized Intestinal Submucosa and its use in an Injectable Tissue Graft," the disclosure of which is incorporated herein by reference, and the teachings of this reference can be adapted for the preparation of fluidized amnion tissue.

Enzymatic digestion of the amnion tissue is conducted under conditions that retain the ability of the endogenous amnion collagen fibers to self assemble. The concentration of the enzyme used is adjusted based on the specific enzyme used, the amount of amnion tissue to be digested, the predetermined time of digestion, the temperature of the reaction, and the desired properties of the final product. In one embodiment about 0.1% to about 0.2% of enzyme (pepsin, for example) is added and the digestion is conducted at 4° C. for 72 hours. However the digestion can be conducted at any temperature ranging from 4 to 37° C. and the digestion times can be adjusted accordingly from 2 to 180 hours. In general, the ratio of the concentration of amnion tissue (hydrated) to total enzyme ranges from about 25 to about 125 and more typically the ratio is about 50, and the digestion is conducted at 4 to 37° C. for 24-72 hours. A person of ordinary skill in the art will recognize that additional ranges of enzyme concentration and treatment times within the explicit ranges above are contemplated and are within the present disclosure.

The enzymes or other disruptive agents used to solubilize the amnion tissue can be removed or inactivated before being used for stent scaffold modification. Also, any disruptive agent, particularly enzymes that remain present and active during storage of the tissue will change the composition and potentially the characteristics of the solution. Enzymes, such as pepsin, can be inactivated with protease inhibitors, a shift to neutral pH, a drop in temperature below 0° C., heat inactivation or through the removal of the enzyme by fractionation. A combination of these methods can be utilized to stop digestion of the amino tissue at a predetermined endpoint, for example the amnion tissue can be immediately frozen and later fractionated to limit the digestion of the amnion tissue.

The amnion tissue is enzymatically digested for a sufficient time to produce a hydrolysate of amnion components. Typically the amnion tissue is treated with one enzyme, however the amnion tissue can be treated with a mixture of enzymes to hydrolyze the structural components of the amnion tissue and prepare a hydrolysate having multiple hydrolyzed amnion components of reduced molecular weight. The length of digestion time is varied depending on the application, and the digestion can be extended to completely solubilize the amnion tissue. In some embodiments, the amnion tissue is partially solubilized to produce an amnion digest composition comprising hydrolyzed amnion components and nonhydrolyzed amnion components.

In one embodiment the digest composition is further manipulated to remove at least some of the nonhydrolyzed components of the amnion. For example, the nonhydrolyzed components can be separated from the hydrolyzed portions by centrifugation. Alternatively, other separation techniques familiar to those skilled in the art, such as filtration, can be used in accordance with this invention. Accordingly, partially solubilized amnion can be filtered or subject to centrifugation to remove insoluble portions of the digest composition and thus form a substantially uniform hydrolysate of amnion tissue. The ionic strength, pH, and molecular cut off of the final solution may need to be adjusted before the solubilized amnion can be used to modify stent scaffold. The solubilized amnion tissue or amnion tissue thus formed can be lyophilized for storage. The lyophilized amnion tissue can be reconstituted and then used as suitable material to modify the stent scaffold. Amnion tubes or sheets can also be formed from the amnion solution.

The solubilized amnion tissue may be able to form an amnion solution or an amnion suspension. The term "solubilized amnion tissue" used herein refers to both solution form and suspension form of amnion. Besides the dip coating and spaying methods, the stent scaffold can also be coated with solubilized amnion tissue using a variety of methods, including electrodeposition. Electrodeposition of solubilized tissue generally is described, for example, in U.S. Pat. No. 5,275,826, above, and U.S. Pat. No. 6,391,052 to Buirge et al., entitled "Stent With Collagen," both of which are incorporated herein by reference.

Other Biocompatible Material

Figures 12A, 12B, 12C:
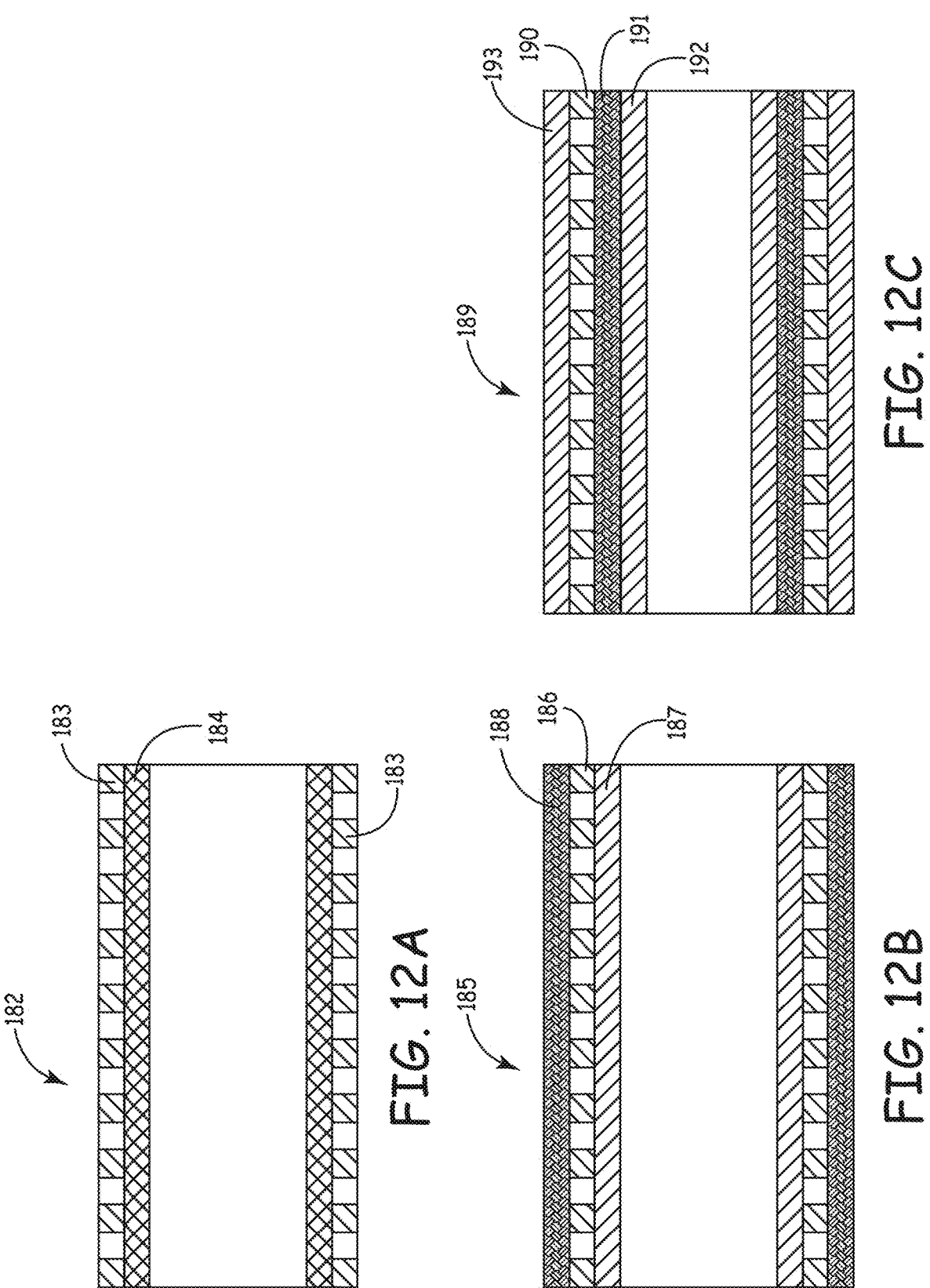
FIG. 12A is a cross sectional view showing the longitudinal cross section of biocompatible stents with a stent scaffold covered with a placental artery or vein as a sleeve.
FIG. 12B is a cross sectional view showing the longitudinal cross section of biocompatible stents with an inner amnion sleeve and an outer polymer sleeve.
FIG. 12C is a cross sectional view showing the longitudinal cross section of biocompatible stents with an outer amnion sleeve, an inner polymer sleeve and an inner amnion sleeve inside the inner polymer sleeve.

Small intestinal submucosa and pericardium from for example bovine, porcine, ovine, or equine sources may be used as biocompatible material alternative to or in conjunction with amnion tissue or placental tissue. Xenograft tissue can be crosslinked, such as with glutaraldehyde, prior to use to kill the cells and remove more extreme rejection responses while maintaining desired mechanical integrity of the tissue. Additionally, chorion tissue, placental artery or vein may be used. For example, FIG. 12A shows a longitudinal cross-sectional view of a biocompatible stent 182 comprises a stent scaffold mesh 183 being lined with a placental artery or vein 184. In some embodiments, materials, such as polyester, e.g., DACRON®, can be used as a support for the amnion tissue.

Biocompatible polymers can similarly be used as a covering for a stent support or a portion thereof. For example, FIG. 12B shows a longitudinal cross section of a biocompatible stent 185 with stent scaffold 186, interior amnion lining 187 and exterior covering 188 made from a polymeric fabric. The polymeric fabric generally may be made from any of the polymeric material listed in the material section above. The fabric may be woven, nonwoven, braided or knitted. The fabric sleeve maybe seamless or have a seam. The fabric may be attached to the stent by mechanical means such as sewing, hooks, barbs, and suture. The fabric may also be attached to the stent by RF welding, ultrasonic welding, thermal bonding, laser welding or adhesive bonding. In one embodiment, the polymeric fabric comprises expanded-polytetrafluoroethylene (ePTFE). FIG. 12C shows a longitudinal cross section of a biocompatible stent 189 with stent scaffold 190 being lined with a polymeric fabric 191. The polymeric fabric layer 191 is in turn lined with an amnion lining 192. The exterior of the stent scaffold 190 is covered with an exterior amnion covering 193. The inner amnion layer and the fabric layer may additionally be fastened together by gluing or sewing. In one embodiment, the polymeric fabric comprises ePTFE.

Stent Scaffold

For vascular stent applications, the stent scaffold can incorporate structural elements from conventional vascular stents. In particular, vascular stents can be designed for appropriate deployment from a lower profile delivery configuration and an expanded deployed configuration. The modified stents generally can have an expanded diameter in the range from about 2 mm to about 50 mm, in further embodiments from about 2.5 mm to about 25 mm, and in other embodiments from about 3 mm to about 10 mm. Also, the modified stents can have a length in the range from about 3 mm to about 100 mm, in further embodiments from about 4 mm to about 85 and in additional embodiments from about 5 mm to about 75 mm. A person of ordinary skill in the art will recognize that additional ranges of stent dimensions within the explicit ranges above are contemplated and are within the present disclosure. The stent scaffold can be formed in an expandable structure by removing material from an approximately tubular element, such as with laser cutting or the like. In some embodiments, a stent scaffold can be formed by assembling structural elements a such as wires, ribbons, molded elements or the like, which can be attached by welding, solder, heat bonding or any other reasonable approach. A stent formed with connected struts is described further in U.S. Pat. No. 7,326,241 to Jang, entitled "Intravascular Stent," incorporated herein by reference.

The stent scaffold may be self expandable and/or mechanically expandable. Self-expanding devices generally comprise a material that expands upon release from a constraint or upon exposure to the temperature within the patient. A device for the delivery of a self expanding stent is described in U.S. Pat. No. 6,090,035 to Campbell et al., entitled "Stent Loading Assembly for a Self-Expanding Stent," incorporated herein by reference. Furthermore, the stent scaffold may be expanded by a balloon, mechanical expansion device or the like. A balloon based delivery system is described further in U.S. Pat. No. 6,293,959 to Miller et al., entitled "Balloon Catheter and Stent Delivery System having Enhanced Stent Retention and Method," incorporated herein by reference.

Figures 13A, 13B:
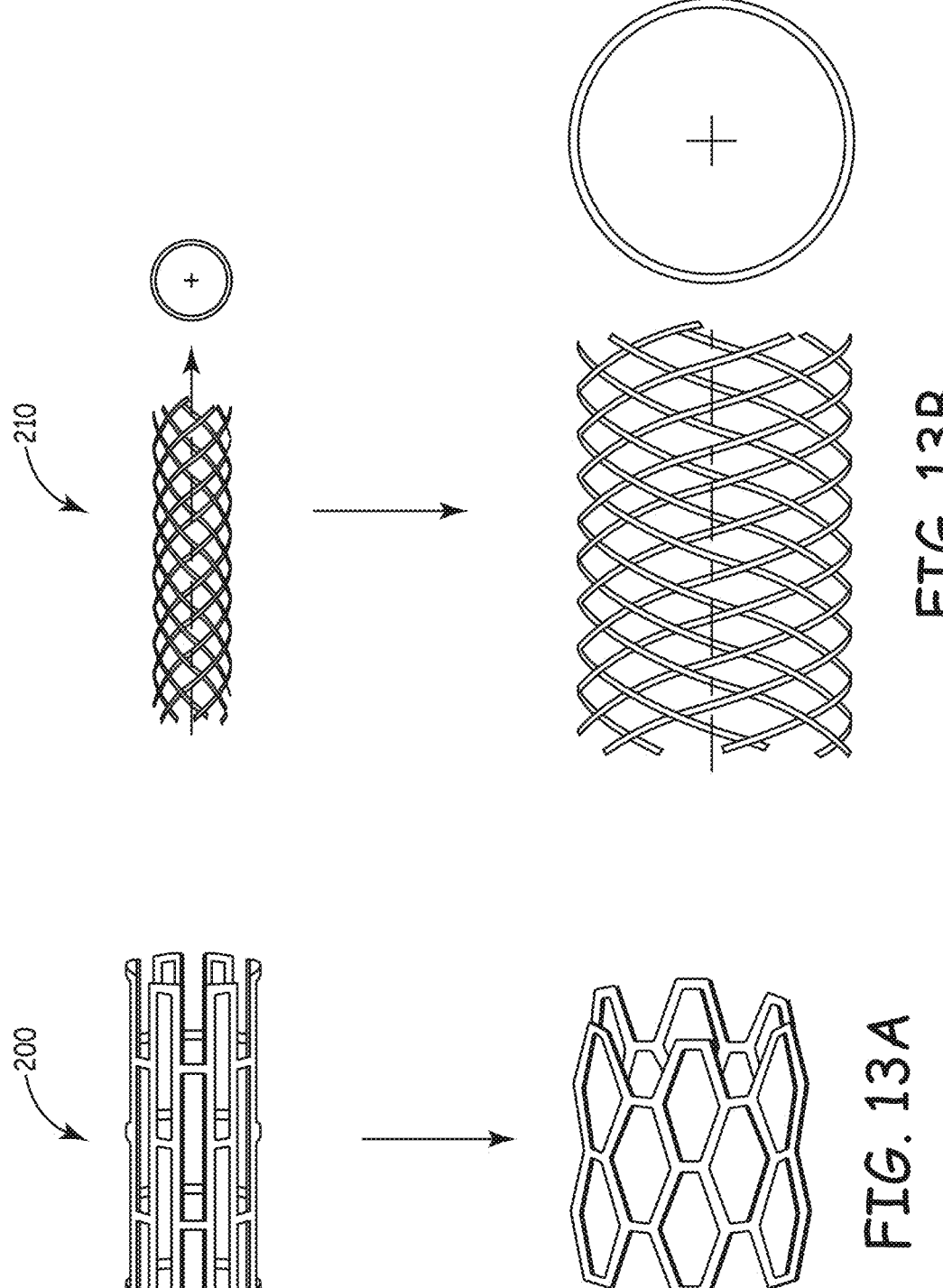
FIG. 13A is a side view of a stent scaffold in unexpanded and expanded states.
FIG. 13B is a side view of a self-expanding stent scaffold in the compressed and expanded states.

In general, the stent scaffold has an unexpanded or compressed configuration and an expanded configuration. Referring to FIG. 13A, stent scaffold 200 in shown in unexpanded and expanded configurations with the unexpanded configuration having a smaller diameter p and with the expanded configuration having a larger diameter p'. FIG. 13B shows a self expanding stent scaffold 210 in a compressed configuration having a smaller cross section diameter and an expanded configuration having a larger cross section diameter. The stent scaffold may be slotted tubular, rolled flat sheet, coiled, or braided.

Figure 14A:
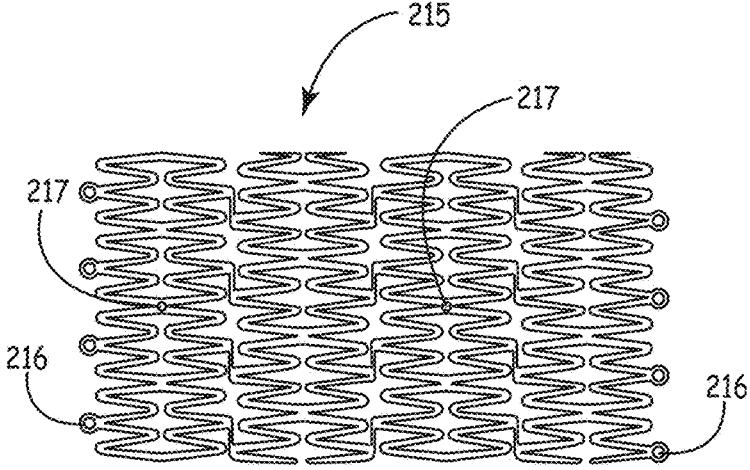
FIG. 14A is a side view of a stent scaffold with eyelets on the ends and in the stent mesh to provide for suture anchoring locations.
Figure 14B:
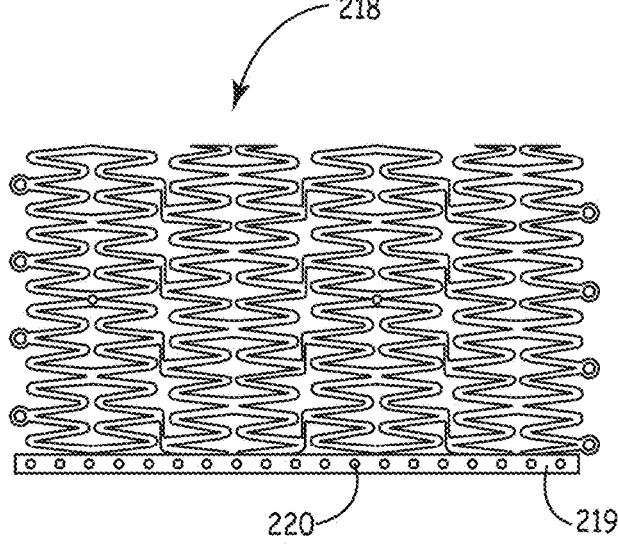
FIG. 14B is a side view of a stent scaffold with additionally a longitudinal bar with eyelets for suture anchoring.
Figure 15:
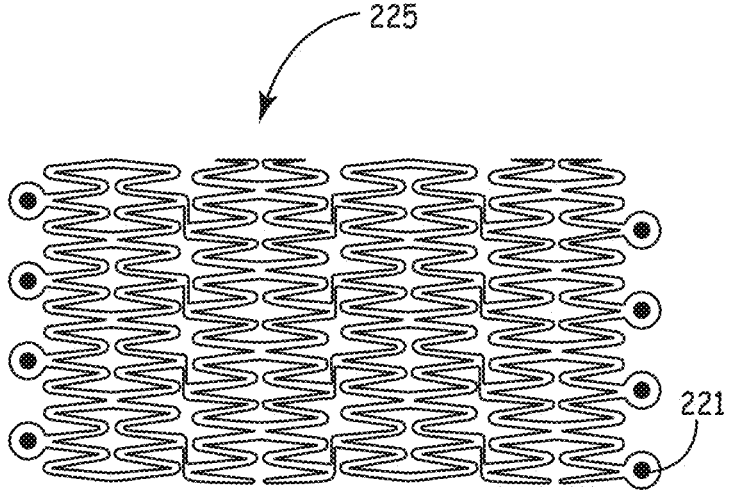
FIG. 15 is a side view of a stent with radiopaque markers.

The stent scaffold may have eyelets to provide for suture anchoring positions. Referring to FIG. 14A, a stent scaffold 215 has eyelets 216 and 217 on the ends and in the stent mesh respectively to provide for suture anchoring locations. FIG. 14B shows a stent scaffold 218 with additionally a longitudinal bar 219 with eyelets 220 for suture anchoring. In some embodiments, radiopaque markers may be present in the stent scaffold. Referring to FIG. 15, a stent scaffold 225 has radiopaque markers 221 at the ends of the scaffold.

The stent scaffold may be made from metals, polymers, or a combination thereof. Metals suitable for stent scaffold include: nickel titanium alloys such as Nitinol; stainless steel alloys such as 304 and 316 L, BioDur® 108 Alloy, Pyromet Alloy® CTX-909, Pyromet® Alloy CTX-3, Pyromet® Alloy 31, Pyromet® Alloy CTX-1, 21Cr-6Ni-9Mn Stainless, 21Cr-6Ni-9Mn Stainless, Pyromet Alloy 350, 18Cr-2Ni-12Mn Stainless, Custom 630 (17Cr-4Ni) Stainless, Custom 465® Stainless, Custom 455® Stainless Custom 450® Stainless, Carpenter 13-8 Stainless, Type 440C Stainless; cobalt chromium alloys such as MP35N, Elgiloy, L605, Carpenter CCM alloy; titanium and titanium alloys, such as Ti-6A1-4V/ELI and Ti-6A1-7Nb, Ti-15Mo; tantalum; tungsten and tungsten alloys; platinum; platinum-iridium alloys; platinum-nickel alloys; niobium; iridium; conichrome; gold and gold alloys. Absorbable metals, such as iron, magnesium, and magnesium alloys, can also be used when the stent scaffold is intended to be absorbable.

Polymers suitable for stent scaffold include: polyether ether ketone (PEEK), polycarbonate, polyolefin, polyethylene, polyether block amide (PEBAX), nylon 6, nylon 6-6, nylon 12, polypropylene, polyester, polyurethane, polytetrafluoroethylene (PTFE), poly(phenylene sulfide) (PPS), poly(butylene terephthalate) (PBT), polysulfone, polyamide, polyimide, poly(p-phenylene oxide) (PPO), acrylonitrile butadiene styrene (ABS), polystyrene, poly(methyl methacrylate) (PMMA), polyoxymethylene (POM), ethylene vinyl acetate, styrene acrylonitrile, and polybutylene. Absorbable polymers such as poly glycolic acid (PGA), polylactide (PLA), poly(ε-caprolactone), poly(dioxanone), and poly(lactide-co-glycolide), can also be used when the stent scaffold is intended to be absorbable. Polymers can be, for example, molded, heat bonded or otherwise appropriately processed to form the desired structure.

Adhesive Materials

Besides liquid amnion, materials such as silicone, polyether block amides (PEBAX), polyurethanes, silicone polyurethane copolymers, bio-adhesives made from amnion or collagen can be used as adhesive material to form the amnion covering or lining and secure the covering or lining onto the stent scaffold. Materials such as polyester, nylon, ePTFE, catgut, and chromic can be used as suturing material.

The biocompatible stent maybe delivered using a catheter. Suitable materials for making such a catheter include silicone, polyether block amide (PEBAX), polyurethane, silicone polyurethane copolymer, nylon such as nylon 6, nylon 6-6, and nylon 12, polyethylene terephthalate (PET), Gore-Tex ePTFE, Kevlar, Spectra, Dyneena, polyvinyl chloride (PVC), polyether ether ketone (PEEK), polycarbonate, polyolefin, polyethylene, polypropylene, polyesters, polyurethanes, polytetrafluoroethylene (PTFE), poly(phenylene sulfide) (PPS), poly(butylene terephthalate) (PBT), polysulfone, polyamide, polyimide, poly(p-phenylene oxide) (PPO), acrylonitrile butadiene styrene (ABS), polystyrene, poly(methyl methacrylate) (PMMA), polyoxymethylene (POM), ethylene vinyl acetate, styrene acrylonitrile, and polybutylene, Methods of Delivery and Deployment of the Biocompatible Stent The biocompatible stent may be delivered using a catheter or the like. The devices generally are introduced into the vessel of the patient using an appropriate approach. For placement into blood vessels conventional percutaneous procedures can be used in which the distal end of the device is placed into the vessel through a small incision with appropriate haemostatic valves and the like to isolate the vessel. The distal end of the catheter can then be navigated to the procedure location, such as a coronary artery.

Figure 16A:
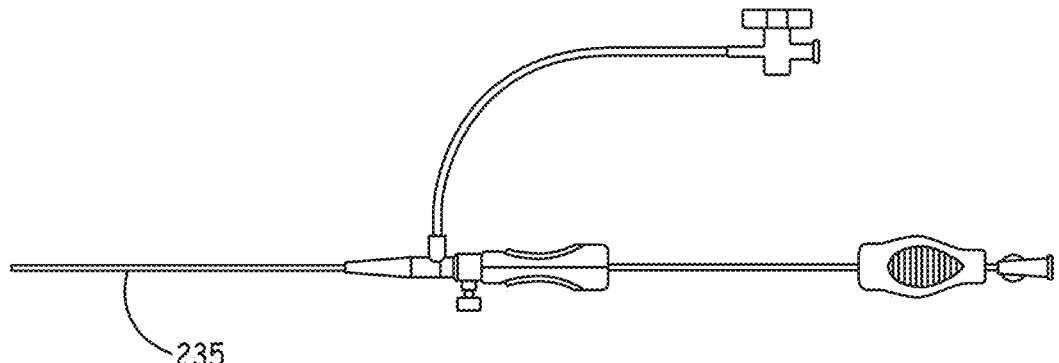
FIG. 16A is a plan view of a delivery catheter for delivering self-expanding stents.
Figure 16B:
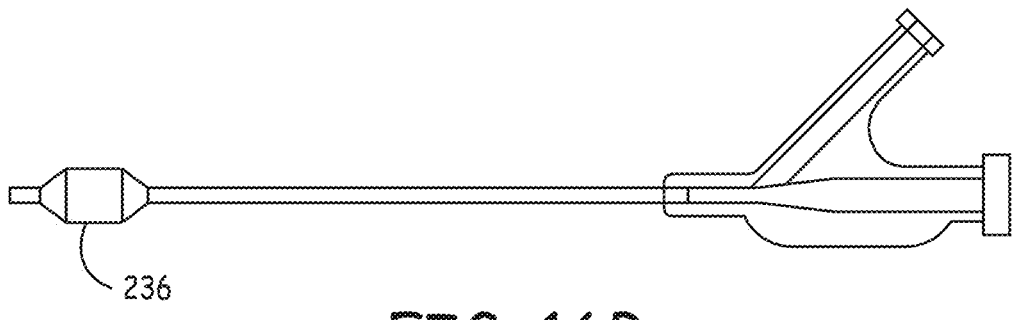
FIG. 16B is a balloon catheter for delivery balloon expandable stents.

Referring to FIG. 16A, a delivery catheter 235 is shown that can be suitable for delivering self-expanding biocompatible stents. FIG. 16B shows a balloon catheter, with balloon 236 expanded, for delivery balloon expandable biocompatible stents. In one embodiment, percutaneous transluminal angioplasty (PTA) balloons may be used. In another embodiment, percutaneous transluminal coronary (PTCA) balloons may be used. The biocompatible stent may be self-expandable, implantable, removable, suitable for topical applications, suitable for temporary implantation, or absorbable.

Because the good stretchability of amnion tissue, biocompatible stent formed from stent scaffold modified with amnion tissue has similar expandability of the unmodified stent scaffold and thus can be similarly delivered and deployed. Stents are typically placed or implanted by a mechanical transluminal procedure. One common procedure for implanting a stent is to first open the region of the vessels with a balloon catheter and then place the stent in a position that bridges the treated portion of the vessel by means of a placement catheter. The stent expands as necessary to an implanted configuration after insertion with the aid of a catheter. Specifically, U.S. Pat. No. 4,733,665 to Palmaz which issued Mar. 29, 1988, discloses a number of stent configurations for implantation with the aid of a catheter. The catheter includes means for mounting and retaining the stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel. U.S. Pat. No. 4,950,227 to Savin et al., which issued on Aug. 21, 1990 is similar, both are incorporated herein by reference.

Another similar U.S. Pat. No. 5,019,090 discloses a generally cylindrical stent and a technique for implanting it using a deflated balloon catheter to position the stent within a vessel. Once the stent is properly positioned the balloon is inflated to press the stent against the inner wall linings of the vessel. The balloon is then deflated and withdrawn from the vessel, leaving the stent in place. U.S. Pat. No. 4,503,569 to Dotter which issued Mar. 12, 1985 discloses a spring stent which expands to an implanted configuration with a change in temperature, is incorporated herein by reference. The spring stent is implanted in a coiled orientation and heated to cause the spring to expand due to the characteristics of the shape memory alloy from which the stent is made. Similarly, U.S. Pat. No. 4,512,338 to Balko et al., which issued Apr. 23, 1985, discloses a shape memory alloy stent and method for its delivery and use other kinds of self-expanding stents are known in the art, is incorporated herein by reference.

U.S. Pat. No. 5,195,984 to Schatz, issued Mar. 23, 1993, describes a typical balloon expansion procedure for an expandable stent. This patent is incorporated in its entirety herein by reference. That patent describes a catheter having an expandable inflatable portion associated therewith. In a conventional manner, the catheter and stent are delivered to a desired location within a body passageway at which it is desired to expand the stent for implantation. Fluoroscopy, and or other conventional techniques may be utilized to insure that the catheter and graft are delivered to the desired location. The stent is then controllably expanded and deformed by controllably expanding the expandable inflatable portion of catheter, typically a balloon. As a result the stent is deformed radially outwardly into contact with the walls of the body passageway. In this regard, the expandable inflatable portion of the catheter may be a conventional angioplasty balloon as is already known in the art. After the desired expansion and deformation of the stent has been accomplished, the angioplasty balloon may be deflated and the catheter removed in a conventional manner from the passageway. Also, this invention is useful in self-expanding stents such as those disclosed in U.S. Pat. Nos. 4,732,152 and 4,848,343, both of which are incorporated herein by reference.

The variable diameter type of stent can be either balloon expandable or self-expanding, both of which are also known in the art. Examples of the former type are shown in U.S. Pat. Nos. 4,733,665, 4,739,762 and 4,776,337, all of which are incorporated herein by reference. The latter type is preferred for the purposes of this invention at present, i.e., self-expanding, particularly those made of Nitinol an example of which is discussed in the U.S. Pat. Nos. 4,503, 569 and 4,512,338, also incorporated herein by reference.

Stent Storage

Tissue modified stent may be sterilized prior to storage. Depending on the length of time beings stored, different storage method could be used. Also, the storage technique can be selected based on whether or not the tissue includes viable cells. For short term storage, i.e. less than a week, the tissue covered stent may be stored in sterile biologically compatible buffers, such as those that are well known in the art. If the tissue does not comprise viable cells, this technique using a suitable buffer would be suitable to store the tissue for moderate periods of time, and the containers can be appropriately marked such that the device can be used with any degradation of the tissue due to the passage of time being within acceptable levels.

The storage of tissue with viable cells can involve more care, but appropriate techniques have been developed for the storage of donor tissue. For example, a storage technique involving near freezing temperatures is described in U.S. Pat. No. 7,029,839 to Toledo-Pereyra et al., entitled "Methods and Solutions for Storing Donor Organs," incorporated herein by reference. Another tissue storage technique involving temperatures near freezing, is described in published U.S. patent application 2009/0286220A to Sheleg et al., entitled "Hypothermic Preservation of Biological Tissues and Cells," incorporated herein by reference.

The devices are sold to appropriate health care professionals for use. The devices are sold with appropriate FDA approved labels explaining proper use of the devices.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

We claim:

1. A method for forming a stent for placement in a vessel of a living subject comprising:
   forming a biocompatible material comprising intact sheet amnion tissue that has not been cryo-preserved at a temperature of −60 to −100° C. and that has been maintained in a hydrated state from harvesting to encapsulation of the stent sufficient to maintain viable cells of the amnion tissue whether or not viable cells are present in the tissue; and
   attaching the biocompatible material to a cylindrical stent scaffold that completely encapsulates the stent scaffold.

2. The method of claim 1 wherein the biocompatible material is rinsed with hypotonic solution to lyse cells.

3. The method of claim 1 wherein the biocompatible material further comprises stem cells.

4. The method of claim 3 wherein the stem cells are native to the sheet amnion tissue.

5. The method of claim 1 wherein the stent scaffold is bioabsorbable.

6. The method of claim 1 wherein the stent scaffold is self-expanding.

7. The method of claim 1 wherein the stent scaffold has a first undeployed configuration and a second deployed configuration wherein the first undeployed configuration of the stent scaffold has a first diameter and the second deployed configuration has a second diameter, and the first diameter is smaller than the second diameter.

8. The method of claim 1 wherein the stent scaffold comprises metal.

9. The method of claim 1 wherein the stent comprises absorbable polymer.

10. The method of claim 9 wherein the absorbable polymer comprises poly glycolic acid (PGA), polylactide (PLA), poly(ε-caprolactone), poly(dioxanone), or poly(lactide-co-glycolide).

11. The method of claim 1 wherein the biocompatible material is in the form of an amnion membrane tube within the stent scaffold with the amnion tissue rolled over the ends of the stent scaffold.

12. The method of claim 1 wherein the stent scaffold is balloon expandable.

13. The method of claim 1 further comprising a thrombolytic agent, an anti-restenosis agent, cellular material, or a combination thereof.

14. The method of claim 1 further comprising cellular material.

15. The method of claim 1 wherein the sheet amnion tissue is in the form of an amnion membrane tube within the stent scaffold with the amnion tissue rolled over the ends of the stent scaffold to encapsulate the stent scaffold.

16. The method of claim 1 wherein the sheet amnion tissue is devoid of viable cells.

17. The method of claim 1 wherein the sheet amnion tissue was stored at temperatures from about −40° C. to about 0° C. during processing.

18. The method of claim 1 wherein the sheet amnion tissue has the epithelium layer removed.

* * * * *

24